US008226983B2

(12) United States Patent
Hirokawa et al.

(10) Patent No.: US 8,226,983 B2
(45) Date of Patent: Jul. 24, 2012

(54) METHOD FOR PRODUCING PULVERIZED ORGANIC COMPOUND PARTICLE

(75) Inventors: Takashi Hirokawa, Chiba (JP); Takahiro Tada, Chiba (JP)

(73) Assignee: Activus Pharma Co., Ltd., Chiba (JP)

( * ) Notice: Subject to any disclaimer, the term of this patent is extended or adjusted under 35 U.S.C. 154(b) by 317 days.

(21) Appl. No.: 12/585,786

(22) Filed: Sep. 24, 2009

(65) Prior Publication Data

US 2010/0016597 A1    Jan. 21, 2010

Related U.S. Application Data

(63) Continuation of application No. PCT/JP2008/056799, filed on Apr. 4, 2008.

(30) Foreign Application Priority Data

Apr. 6, 2007 (JP) ................................ 2007-100902
Aug. 10, 2007 (JP) ................................ 2007-210370

(51) Int. Cl.
*A61K 9/14* (2006.01)
(52) U.S. Cl. ....................................................... 424/489
(58) Field of Classification Search .................. 424/489
See application file for complete search history.

(56) References Cited

U.S. PATENT DOCUMENTS

| 5,626,662 | A | 5/1997 | Urban |
| 6,284,282 | B1 | 9/2001 | Maa et al. |
| 2002/0003179 | A1 | 1/2002 | Verhoff et al. |
| 2002/0047058 | A1 | 4/2002 | Verhoff et al. |
| 2004/0258757 | A1* | 12/2004 | Bosch et al. .................. 424/489 |

FOREIGN PATENT DOCUMENTS

| JP | 58-17167 | A | 2/1983 |
| JP | 03-066613 | A | 3/1991 |
| JP | 03-131355 | A | 6/1991 |
| JP | 04-295420 | A | 10/1992 |
| JP | 06-228454 | A | 8/1994 |
| JP | 2642486 | B2 | 5/1997 |
| JP | 2683458 | B2 | 8/1997 |
| JP | 10-330799 | A | 12/1998 |
| JP | 11-100317 | A | 4/1999 |
| JP | 2002-511398 | A | 4/2002 |
| JP | 2002-518318 | A | 6/2002 |
| JP | 2003-286105 | A | 10/2003 |
| JP | 2003-342493 | A | 12/2003 |
| JP | 3602546 | B2 | 10/2004 |
| JP | 2004-330078 | A | 11/2004 |
| JP | 2005-008806 | A | 1/2005 |
| JP | 2006-089386 | A | 4/2006 |
| JP | 2006-182992 | A | 7/2006 |
| JP | 2006-255519 | A | 9/2006 |
| WO | WO 2006/087919 | A1 | 8/2006 |
| WO | WO 2006/108637 | A2 | 10/2006 |

OTHER PUBLICATIONS

Office Action dated Oct. 17, 2011 in corresponding CN patent application No. 2008800084620 (and English translation).
Extended European Search Report dated Apr. 22, 2010 issued from the European Patent Office in corresponding European patent application No. 08739905.1-1219.
Kuwahara, Y., "Pulverizing Process and Contamination of Pulverizing Area," *Advanced Pulverizing Technology and Its Application*, NGT, 81-88 (2005) (partial English translation of (6) Summary of this section; discussed on pp. 7 and 12 of the Specification).
PCT International Search Report mailed on Jul. 8, 2008 for the corresponding International patent application No. PCT/JP2008/056799.

* cited by examiner

*Primary Examiner* — James H. Alstrum-Acevedo
*Assistant Examiner* — Thor Nielsen
(74) *Attorney, Agent, or Firm* — Posz Law Group, PLC

(57) ABSTRACT

Disclosed is a method for producing pulverized particles of a crystalline organic compound which is poorly water-soluble. Also disclosed is a pulverized organic compound particle produced by such a method. Specifically disclosed is a method for producing a poor water solubility organic compound particle for medical use, which is characterized in that a poor water solubility organic compound for medical use is mixed with a physiologically acceptable salt and a physiologically acceptable polyol, and subjected to wet milling. Also specifically disclosed is a poor water solubility organic compound particle for medical use, which is produced by such a production method.

14 Claims, 8 Drawing Sheets ived from the fact that the particles are finely pulverized, # METHOD FOR PRODUCING PULVERIZED ORGANIC COMPOUND PARTICLE

CROSS-REFERENCE TO RELATED APPLICATIONS

The present patent application claims priority from Japanese Patent Application No. 2007-100902 filed in Japan on Apr. 6, 2007, and Japanese Patent Application No. 2007-210370 filed on Aug. 10, 2007, the disclosures of which are incorporated herein by reference. The disclosures of the patents, patent applications and documents cited in the present application are incorporated herein by reference.

TECHNICAL FIELD

The present invention relates to a method for producing finely pulverized organic compound particles, and particularly, relates to organic compound fine particles for medical use, which are poorly water-soluble, and a method for producing organic compound fine particles for medical use.

BACKGROUND

Development of a preparation containing a poor water solubility organic compound as an active ingredient is usually difficult. For example, a significant number of oral preparations of poor water solubility or insoluble organic compounds have poor absorbability from the digestion tract or the like, and fluctuations are large, so that it is difficult to obtain stable drug efficacies. Most of the candidate organic compounds for new drugs, from which very excellent efficacies could be expected if the compounds had been appropriately absorbed into the body, have problems such as the interruption of development or lengthening of the development period, due to their low bioavailability. On the other hand, even among the compounds for medical use that have already been approved as drugs, there are many poor water solubility organic compounds. For example, one-third or more of the drugs listed in the US Pharmacopoeia are poorly soluble or insoluble in water. Thus, it can also be expected to improve the existing preparations to preparations having more excellent medicinal efficacy, by improving the bioavailability of these poor water solubility organic compounds. Therefore, development of a method for improving the bioavailability of such a poor water solubility organic compound is strongly desired.

Heretofore, in regard to the preparations containing a poor water solubility organic compound as an active ingredient, a method of producing such a preparation by solubilizing the organic compound with an organic solvent or an aqueous solution containing a surface active agent, has been frequently employed. However, the organic solvents that are included in the package inserts of the existing many injectable preparations of poor water solubility organic compounds, are highly possible to bring about events that are not preferable from a medical point of view. Thus, preparations that do not contain these solvents have been demanded.

On the other hand, concomitantly with the recent development in nanotechnology, high expectations can be placed on the applied research on nanoparticles alone or assemblages thereof, and the development of the particle pulverization technology is popular in many industrial fields. In the field of medicine as well, a method of finely pulverizing a poor water solubility organic compound into nanoparticles is attracting attention as a method for improving the bioavailability of the organic compound. When particles are finely pulverized, the specific surface area of the particles is drastically increased, and in many cases, excellent characteristics that could not be predicted come to be discovered. It is conceived that a progress in the technology of pulverization now enables development of preparations for medical use having preferable characteristics that could not be seen hitherto.

Since it is expected to have improvements in the bioavailability of a poor water solubility organic compound for medical use or in the suitability to formulation by finely pulverizing the organic compound, some finely pulverized, poor water solubility organic compounds are known.

For example, there is known a preparation containing a steroid or a steroid derivative, of which the center of the particle size distribution is 0.005 µm to 5 µm, and the 90% median diameter of the particle size distribution is 10 µm (see, for example, Patent Document 1). However, the dispersed particles described in this document have a broad particle size distribution, and the stability of the suspension is decreased by the influence of coarse particles that are present, mixed in an amount of a few percents. Furthermore, although the preparation is subjected to a sterilization treatment using a 0.2-µm membrane filter for the purpose of carrying out the production of eye drops and injectable preparations efficiently, the permeability is markedly decreased due to the influence of these coarse particles, and there is a problem that the sterilization treatment using a 0.2-µm membrane filter is difficult.

Several methods have been disclosed as the method of pulverizing such a poor water solubility organic compound for medical use. For example, there is disclosed (1) a method of adding a non-crosslinked surface modifying agent to a organic compound having low solubility, and thereby making the particle size of the organic compound small by a mechanical means (see, for example, Patent Document 2). Through this method, pulverized particles of an organic compound onto which a sufficient amount of a surface modifying agent is adsorbed so as to maintain the state of the average particle size being less than about 400 mm, can be produced. However, the particles essentially necessitate the surface modifying agent, and the Examples describe only the technique of nanolization by a bead mill. Thus, in this case, there was a problem that contamination is prone to occur under the effect of the abrasion of the beads.

As for the method of using the supercritical technique, for example, there is disclosed (2) a method for producing a pulverous preparation of a biologically active compound having a size at the (sub)micron level, the method including (i) a process for dissolving the biologically active compound in a compressed gas, liquid or supercritical fluid containing a surface modifying agent under elevated pressure, or dissolving the biologically active compound in compressed dimethyl ether optionally containing a surface modifying agent; (iia) a process for rapidly expanding the compressed solution of the process (i), and thereby precipitating the dissolved compound; or (iib) a process of spraying the compressed solution of the process (i) into an antisolvent phase optionally containing a surface modifying agent under reduced pressure, under atmospheric pressure or under elevated pressure; and (3) a process for optionally converting the antisolvent phase of the process (iib) to a pulverous preparation using a conventional powder process technique (see, for example, Patent Document 3). Through the method, finely pulverized particles of the sub-micron level having an average particle diameter of 5 to 5,000 nm, and preferably 200 to 1,000 nm, can be produced.

As another method using the supercritical technique, there is disclosed (3) a method for preparing submicron particles of a water-insoluble compound, particularly a drug, while simultaneously stabilizing the fine particulate suspension with the molecules of a surface modifying agent, by dissolving a water-insoluble compound in a liquefied gas, and rapidly injecting to expand the compressed solution of the compound and the surface modifying agent into an aqueous medium, or optionally by homogenizing the aqueous suspension thus prepared with a high pressure homogenizer (see, for example, Patent Document 4). In these methods using the supercritical technique, the organic compound is dissolved in an appropriate solvent or liquefied gas under supercritical or near-critical conditions, and the mixed liquid is ejected while expanding from a nozzle into a reduced pressure part, a gas or a liquid, to evaporate the solvent. Therefore, control of the production of fine particles is very difficult, and the system needs to be under a high pressure environment in order to establish the supercritical or near-critical conditions, resulting in high production costs, which is not preferable.

Furthermore, as a method of using a hard medium such as beads formed of ceramics, glass or steel, for example, there is disclosed (4) a method of adjusting the average particle diameter of a solid agrochemical active ingredient to 1 to 15 μm, by mixing particulate materials of the solid agrochemical active ingredient which is ductile and malleable at normal temperature and exhibits solidifiability even under storage at a temperature below melting point, a basic white carbon and a porous material, and impact grinding the mixture with a pin mill a hammer mill or the like, or milling the mixture in a high speed air stream with an air mill or the like (see, for example, Patent Document 5). There is also disclosed (5), an organic compound for ultraviolet absorbent having an average particle size in the range of 0.01 to 2 μm, which have been pulverized using a milling apparatus such as a rotary ball mill, as a composition for protecting the skin from sunlight or ultraviolet radiation (see, for example, Patent Document 6). In addition, (6) a method of micronizing a crude polycyclic organic pigment, by preliminarily milling a crude coarse organic pigment by dry milling, and wet-milling the resulting micronized pigment in an aqueous suspension in a stirred ball mill which is operated at a power density of more than 2.5 kW per liter of milling space and a peripheral stirrer speed of more than 12 m/s under the action of a grinding medium having a diameter of 1 mm or less (see, for example, Patent Document 7), and the like are disclosed. However, in these methods using hard media, the abrasion powder generated by the abrasion of the balls or the mill vessel at the time of stirring and milling, is incorporated into the pulverized organic compound particles, and therefore, there has been a problem of so-called contamination (see, for example, Non-Patent Document 1).

As a method of pulverizing a poorly soluble drug by impact grinding, there is disclosed (7) a method of producing ultrafine particles having an average particle size of 1 μm or less, by subjecting 2.5 parts by weight of a saccharide or a mixture with a sugar alcohol with respect to 1 part by weight of a poorly soluble drug, to grinding by high-speed stirring or impact grinding (see, for example, Patent Document 8). However, this method has a problem that it is difficult to prevent the generation of heat due to impact, in addition to the problem of the contamination by abrasion powder. Furthermore, due to the characteristics of the impact grinding apparatus, crystalline organic compounds are likely to become amorphous, and in the case where it is desired to maintain the crystal structure of the organic compounds, the method is unsuitable.

There are also disclosed methods of wet milling an organic compound without using a hard medium, so as to prevent the contamination by abrasion powder. For example, as a method for producing odorless silk fine particles, there is disclosed (8) a method of adding roast salt and diethylene glycol to a purified silk fiber powder, kneading the ingredients, and triturating the mixture into a powder having a size of 1 to 2 μm (see, for example, Patent Document 9). As a method for finely pulverizing a composition for food, for example, there is disclosed (9) a method of dispersing coarse particles in a dispersion medium, subsequently adding a powder of a food additive that is insoluble or poorly soluble in the dispersion medium, to the dispersion liquid, and pulverizing the mixture in a wet pulverizer (see, for example, Patent Document 10), or the like. In addition, as methods of pulverizing a pigment, (10) a method of wet grinding crude dioxazine together with an inorganic salt and an organic liquid such as an alcohol or a polyol (see, for example, Patent Document 11), (11) a method for conditioning a polycyclic pigment, by adding to a crude pigment, a solid grinding aid selected from the group consisting of sodium chloride, sodium sulfate and aluminum sulfate, and a glycol or a mixture of glycols, and treating the pigment in the presence of a metal halide (see, for example, Patent Document 12), and the like are disclosed.

However, the magnesium chloride included in the roast salt that is used in the method of (8), is decomposed during the heating process, and generates poorly soluble basic magnesium chloride. It is difficult to eliminate the basic magnesium chloride from finely pulverized organic compound particles, and the basic magnesium chloride causes contamination as does the abrasion powder. Furthermore, since the fine powder of food obtained by the method of (9) has an average particle diameter of about 5 μm, the method is not very satisfactory as a method for finely pulverizing an organic compound for medical use.

The methods of (10) and (11) describe that pigments having more excellent characteristics compared to conventional pigments can be produced, but it is unclear regarding the degree of fine pulverization, or whether the methods are fine pulverization methods that are applicable to organic compounds for medical use. Particularly, in regard to organic compounds that are active ingredients of pharmaceutical products, it is required that such a compound be finely pulverized while maintaining the crystal form. However, since dissolution of the organic compound in a medium liquid brings about dissolution and re-elution even with a trace amount, thus resulting in a crystal form that is different from the form prior to pulverization, or an amorphous form. Thus, it is known that selection of the medium liquid is very difficult (Pharmaceutical Development and Technology, Vol. 9, No. 1, pp. 1-13 (2004)). The organic pigment pulverized by the solvent-salt milling method described in (1) often develops a color due to the crystal structure, and the chemical structure has fewer substituents and high planarity of the molecule, thus giving a compact crystal structure. For this reason, there are many high melting point compounds (melting point being 350° C. or higher), and many of the compounds are characterized by having low solubility in solvents. The methods of (10) and (11) are conceived to be truly usable because the methods are used for pulverizing pigments, which have particularly low solubility even among poorly soluble organic compounds. Thus, in the case of applying these methods to an organic compound for medical use which, in many cases, has markedly different characteristics such as a sparse crystal lattice, low melting point or high solubility in solvents, as compared to pigments, it has been regarded such that the organic compound for medical use dissolves out in the solvent, and cannot be finely pulverized.

In addition, as a method which does not use a pulverization apparatus, for example, (12) a method of producing porous particles having an average particle diameter of 6 to 8 μm and have excellent aerodynamic properties by freeze-spray drying a protein, and using the particles in an inhalant, is disclosed (see, for example, Patent Document 13).

In the method of (12), since fine pulverization is carried out by freeze-spray drying a compound that has been dissolved in a solvent, if the solvent is not a solvent capable of subliming by freeze-drying, it is difficult to eliminate the solvent from the resulting finely pulverized organic compound particles. Therefore, for compounds other than physiologically acceptable ones, such as a protein, and can be dissolved in a solvent capable of freeze-drying, finely pulverized organic compound particles cannot be produced, even if the method is applied. Also, in the case of carrying out fine pulverization using this method, sufficiently small particles cannot be obtained, and fine particles having excellent suspension stability and permeability through 0.2-μm membrane, could not be produced.

Patent Document 1: Japanese Patent Application Laid-Open (JP-A) No. 2006-89386

Patent Document 2: Japanese Patent No. 3602546

Patent Document 3: Japanese Patent Application National Publication No. 2002-511398

Patent Document 4: Japanese Patent Application National Publication No. 2002-518318

Patent Document 5: JP-A No. 2003-286105

Patent Document 6: JP-A No. 11-100317

Patent Document 7: U.S. Pat. No. 5,626,662

Patent Document 8: Japanese Patent No. 2642486

Patent Document 9: JP-A No. 2006-182992

Patent Document 10: JP-A No. 2004-330078

Patent Document 11: Japanese Patent No. 2683458

Patent Document 12: JP-A No. 58-17167

Patent Document 13: U.S. Pat. No. 6,284,282

Non-Patent Document 1: Kuwahara Yoshitaka, "Pulverization Process in Fine Pulverization Region and Contamination", Cutting-Edge Pulverization Technologies and Applications, NGT (2005), p. 81-88.

SUMMARY

Thus, it is an object of the present invention to provide a poor water solubility organic compound for medical use, having a particle diameter and/or a particle size distribution that allows sufficient exhibition of the effects obtained by nanolization, such as long-term stability, bioavailability or sterilizing membrane permeability. Another object of the present invention is to provide a poor water solubility composition for medical use, which composition is a poor water solubility organic compound for medical use having a particle diameter and/or a particle size distribution that allows sufficient exhibition of the effects obtained by nanolization, such as long-term stability, bioavailability or sterilizing membrane permeability, and which composition does not contain a surface active agent. Another object of the present invention is to obtain porous particles including the assemblages of a powder of a poor water solubility organic compound for medical use, which particles have excellent characteristics as an inhalant, an injectable preparation and/or an oral preparation. Another object of the present invention is to provide a method for producing finely pulverized organic compound particles, which method is capable of finely pulverizing a poor water solubility organic compound useful for medical use, in a physiologically safe manner, and is also applicable to industrial production. Another object of the present invention is to provide a method of finely pulverizing an organic compound for medical use at low production costs. Another object of the present invention is to provide a method for performing fine pulverization while maintaining the crystal form or amorphous form of the organic compound for medical use that the compound had before the fine pulverization. In particular, another object of the present invention is to provide a method for producing fine particles of a poor water solubility organic compound for medical use, having a particle diameter and/or particle size distribution that allows sufficient exhibition of the effects obtained by nanolization, such as long-term stability, bioavailability or sterilizing membrane permeability. Another object of the present invention is to provide a method for producing finely pulverized organic compound particles, which method is capable of finely pulverizing a poor water solubility crystalline organic compound useful as a drug for agrochemicals, a composition for cosmetics, a composition for food or the like, in a physiologically safe manner, and which method is also applicable to industrial production; and finely pulverized organic compound particles obtained by the production method.

Means for Solving the Problems

The present inventors devotedly conducted research to solve the above-described problems, and as a result, they found that when a physiologically acceptable salt and a physiologically acceptable polyol are added and mixed with an organic compound (poor water solubility organic compound for medical use) having a melting point of 80 degrees C. or more, the organic compound can be efficiently pulverized, and when the salt and the polyol are removed after pulverization, finely pulverized organic compound particles (poor water solubility organic compound fine particles for medical use) having a very small average particle diameter can be produced while maintaining the crystal structure. Thus, the inventors completed the present invention.

Specifically, the present invention relates to a poor water solubility organic compound powder for medical use having an average particle size of 500 nm or less, porous fine particles which are aggregates of the powder, a composition for medical use containing the fine particles, and a method for pulverizing poor water solubility organic compound crystals for medical use. More specifically, the present invention relates to the inventions described in the following (1) to (53).

(1) Poor water solubility organic compound fine particles for medical use, having an average particle diameter of 600 nm or less;

(2) Poor water solubility organic compound fine particles for medical use according to (1), wherein the average particle diameter is 10 nm to 300 nm;

(3) Poor water solubility organic compound fine particles for medical use according to (1) or (2), wherein the poor water solubility organic compound for medical use is an organic compound having a melting point of 80 degrees C. or more;

(4) Poor water solubility organic compound fine particles for medical use according to any one of (1) to (3), wherein the ratio of particles having a diameter of 0.2 μm or less is 70% or more;

(5) Poor water solubility organic compound fine particles for medical use according to any one of (1) to (4), wherein the 90% median diameter is 600 nm or less;

(6) Poor water solubility organic compound fine particles for medical use according to any one of (1) to (5), wherein the poor water solubility organic compound for medical use is a crystalline compound;

(7) Poor water solubility organic compound fine particles for medical use according to any one of (1) to (6), wherein the poor water solubility organic compound includes no surface active agent;

(8) Poor water solubility organic compound fine particles for medical use according to any one of (1) to (7), wherein the poor water solubility organic compound for medical use is one or more organic compounds selected from the group consisting of nifedipine, nicardipine, nimodipine, dipyridamole, disopyramide, prazosin hydrochloride, prednisolone, cortisone acetate, dexamethasone, betamethasone, beclometasone dipropionate, fluticasone propionate, budesonide, fluocinolone acetonide, indomethacin, naproxen, ketoprofen, 7-(3,5-dimethoxy-4-hydroxycinnamoylamino)-3-octyloxy-4-hydroxy-1-methyl-2(1H)-quinolinone, phenytoin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazone, phenprobamate, mequitazine, bisbentiamin, mitomycin C, bicalutamide, paclitaxel, ubenimex, dacarbazine, fluconazole, miconazole, rifampicin, triamcinolone acetonide, clemastine fumarate, pranlukast hydrate, zafirlukast, fenofibrate, dihydroxybenzophenone, dihydrocholesterol, β-carotene, propyl gallate, cinnamic acid, saccharin, folic acid and maltol;

(9) Poor water solubility organic compound fine particles for medical use according to any one of (1) to (8), wherein the poor water solubility organic compound for medical use is indomethacin, and has an average particle diameter of 240 nm or less;

(10) Poor water solubility organic compound fine particles for medical use according to any one of (1) to (8), wherein the poor water solubility organic compound for medical use is nifedipine, and has an average particle diameter of 500 nm or less;

(11) Poor water solubility organic compound fine particles for medical use according to any one of (1) to (8), wherein the poor water solubility organic compound for medical use is cortisone acetate, and has an average particle diameter of 500 nm or less.

(12) Poor water solubility organic compound fine particles for medical use according to any one of (1) to (8), wherein the poor water solubility organic compound for medical use is beclometasone dipropionate, and has an average particle diameter of 500 nm or less;

(13) Poor water solubility organic compound fine particles for medical use according to any one of (1) to (8), wherein the poor water solubility organic compound for medical use is 7-(3,5-dimethoxy-4-hydroxycinnamoylamino)-3-octyloxy-4-hydroxy-1-methyl-2(1H)-quinolinone, and has an average particle diameter of 170 nm or less;

(14) Poor water solubility organic compound fine particles for medical use according to any one of (1) to (8), wherein the poor water solubility organic compound for medical use is miconazole, and has an average particle diameter of 500 nm or less;

(15) Poor water solubility organic compound fine particles for medical use according to any one of (1) to (8), wherein the poor water solubility organic compound for medical use is ketoprofen, and has an average particle diameter of 500 nm or less.

(16) Poor water solubility organic compound fine particles for medical use according to any one of (1) to (8), wherein the poor water solubility organic compound for medical use is fluticasone propionate, and has an average particle diameter of 300 nm or less;

(17) Poor water solubility organic compound fine particles for medical use according to any one of (1) to (8), wherein the poor water solubility organic compound for medical use is pranlukast hydrate, and has an average particle diameter of 300 nm or less;

(18) Poor water solubility organic compound fine particles for medical use according to any one of (1) to (8), wherein the poor water solubility organic compound for medical use is dexamethasone, and has an average particle diameter of 300 nm or less;

(19) Poor water solubility organic compound fine particles for medical use according to any one of (1) to (8), wherein the poor water solubility organic compound for medical use is zafirlukast, and has an average particle diameter of 298 nm or less;

(20) Poor water solubility organic compound fine particles for medical use according to any one of (1) to (8), wherein the poor water solubility organic compound for medical use is fenofibrate, and has an average particle diameter of 500 nm or less;

(21) Poor water solubility organic compound fine particles for medical use according to any one of (1) to (20), wherein the 90% median diameter is 500 nm or less;

(22) A powder or water-containing solid matter containing the poor water solubility organic compound fine particles for medical use according to any one of (1) to (21);

(23) A composition for medical use containing the poor water solubility organic compound fine particles for medical use according to any one of (1) to (21), as an active ingredient;

(24) Porous fine particles consisted of assemblages of the poor water solubility organic compound fine particles for medical use according to any one of (1) to (22);

(25) Porous fine particles according to (24), wherein the specific surface area measured by the BET method is 3 to 300 $m^2/g$;

(26) A composition for medical use, containing the porous fine particles according to (24) or (25), as an active ingredient;

(27) A method for producing poor water solubility organic compound fine particles for medical use, the method including mixing a poor water solubility organic compound for medical use with a physiologically acceptable salt and a physiologically acceptable polyol, and wet-milling the organic compound;

(28) A method for producing poor water solubility organic compound fine particles for medical use according to (27), wherein the poor water solubility organic compound for medical use is an organic compound having a melting point of 80 degrees C. or more;

(29) A method for producing poor water solubility organic compound fine particles for medical use according to (27) or (28), wherein the poor water solubility organic compound for medical use is an organic compound having a melting point of 80 degrees C. or more and 350 degrees C. or less;

(30) A method for producing poor water solubility organic compound fine particles for medical use according to any one of (27) to (29), wherein the poor water solubility organic compound for medical use is a crystalline compound;

(31) A method for producing poor water solubility organic compound fine particles for medical use according to any one of (27) to (30), further including excluding the salt and/or the polyol;

(32) A method for producing poor water solubility organic compound fine particles for medical use according to any one of (27) to (31), wherein the physiologically acceptable polyol includes a viscosity modifier;

(33) A method for producing poor water solubility organic compound fine particles for medical use according to (32), wherein the physiologically acceptable polyol includes a viscosity modifier so that the viscosity of the polyol may be 1000 mPa·s or more at 20 degrees C.;

(34) A method for producing poor water solubility organic compound fine particles for medical use according to (32) or (33), wherein the viscosity modifier is one or more viscosity modifiers selected from the group consisting of citric acid, DL-malic acid, D-sorbitol, D-mannitol, maltitol, maltose, tartaric acid, glucose, erythritol, xylitol, D-xylose, trehalose, fructose, lactic acid, lactose, glycine, urea, maleic acid or malonic acid;

(35) A method for producing poor water solubility organic compound fine particles for medical use according to any one of (27) to (34), wherein a solid pulverization aid including glass, metal, ceramics or a hard polymer is not added;

(36) A method for producing poor water solubility organic compound fine particles for medical use according to any one of (27) to (35), wherein a slid pulverization aid is not added;

(37) A method for producing poor water solubility organic compound fine particles for medical use according to any one of (27) to (36), wherein the polyol is glycerin, propylene glycol, dipropylene glycol or polyethylene glycol;

(38) A method for producing poor water solubility organic compound fine particles for medical use according to any one of (27) to (37), wherein the salt is one or more salts selected from the group consisting of sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate and dipotassium hydrogen phosphate;

(39) A production method according to any one of (27) to (38), wherein the salt is sodium chloride, and the polyol is glycerin;

(40) A method for producing poor water solubility organic compound fine particles for medical use according to any one of (27) to (39), including adding no surface active agent;

(41) A method for producing poor water solubility organic compound fine particles for medical use according to any one of (27) to (40), wherein the solubility of the poor water solubility organic compound for medical use in the polyol is 10% (mass/volume) or less, and the solubility of the salt in the polyol is 10% (mass/volume) or less;

(42) A method for producing poor water solubility organic compound fine particles for medical use according to any one of (27) to (41), wherein the poor water solubility organic compound for medical use is one or more organic compounds selected from the group consisting of nifedipine, nicardipine, nimodipine, dipyridamole, disopyramide, prazosin hydrochloride, prednisolone, cortisone acetate, dexamethasone, betamethasone, beclometasone dipropionate, fluticasone propionate, budesonide, fluocinolone acetonide, indomethacin, naproxen, ketoprofen, 7-(3,5-dimethoxy-4-hydroxycinnamoylamino)-3-octyloxy-4-hydroxy-1-methyl-2(1H)-quinolinone, phenytoin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazone, phenprobamate, mequitazine, bisbentiamin, mitomycin C, bicalutamide, paclitaxel, ubenimex, dacarbazine, fluconazole, miconazole, rifampicin, triamcinolone acetonide, clemastine fumarate, pranlukast hydrate, zafirlukast, fenofibrate, dihydroxybenzophenone, dihydrocholesterol, β-carotene, propyl gallate, cinnamic acid, saccharin, folic acid and maltol;

(43) A method for producing poor water solubility organic compound fine particles for medical use according to any one of (27) to (42), wherein the wet-milling is carried out using one apparatus selected from the group consisting of a kneader, a twin-roll, a triple-roll, a fret mill and a disk blade kneader-disperser;

(44) A method for producing poor water solubility organic compound fine particles for medical use according to any one of (27) to (43), wherein the average particle diameter of the produced poor water solubility organic compound fine particles for medical use is 600 nm or less;

(45) A method for producing poor water solubility organic compound fine particles for medical use according to any one of (27) to (44), wherein the ratio of particles having a diameter of 0.2 μm or less in the produced poor water solubility organic compound fine particles for medical use is 70% or more, or the 90% median diameter is 500 nm or less;

(46) A method for producing poor water solubility organic compound fine particles for medical use according to any one of (27) to (45), wherein the produced poor water solubility organic compound fine particles for medical use maintain the crystal form that the particles have before being finely pulverized;

(47) Poor water solubility organic compound fine particles for medical use obtained by the method for producing poor water solubility organic compound fine particles for medical use according to any one of (27) to (46);

(48) A powder including the poor water solubility organic compound fine particles for medical use according to (47);

(49) A water-containing solid matter including the poor water solubility organic compound fine particles for medical use according to (47);

(50) An aqueous dispersion including the poor water solubility organic compound fine particles for medical use according to (47);

(51) An aqueous dispersion according to (50), further including an additive for preventing secondary aggregation;

(52) A pharmaceutical composition including the poor water solubility organic compound fine particles for medical use according to (47), as an active ingredient; and

(53) A pharmaceutical composition, which is produced into porous particles having an average particle diameter of 1 to 30 am, by suspending the poor water solubility organic compound fine particles for medical use according to (47) in water, and then carrying out a spray freeze-drying treatment.

In another aspect, the present invention relates to the following:

(54) A method for producing finely pulverized organic compound particles, the method including adding a physiologically acceptable salt and a physiologically acceptable polyol to an organic compound having a melting point of 80 degrees C. or more (preferably, 84 degrees C. or more), wet-milling the organic compound, and then excluding the salt and the polyol;

(55) A method for producing finely pulverized organic compound particles according to (54), wherein the solubility of the organic compound in the polyol is 10% (mass/volume) or less, and the solubility of the salt in the polyol is 10% (mass/volume) or less;

(56) A method for producing finely pulverized organic compound particles according to (54) or (55), wherein the average particle diameter of the finely pulverized organic compound particles is 600 nm or less;

(57) A method for producing finely pulverized organic compound particles according to any one of (54) to (56), wherein the average particle diameter of the finely pulverized organic compound particles is 500 nm or less;

(58) A method for producing finely pulverized organic compound particles according to any one of (54) to (57), wherein the average particle diameter of the finely pulverized organic compound particles is 300 nm or less;

(59) A method for producing finely pulverized organic compound particles according to any one of (54) to (58), wherein the salt is one or more salts selected from the group consisting of sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate and dipotassium hydrogen phosphate;

(60) A method for producing finely pulverized organic compound particles according to any one of (54) to (59), wherein the polyol is one or more polyols selected from the group consisting of glycerin, propylene glycol, dipropylene glycol, polyethylene glycol and diethylene glycol;

(61) A method for producing finely pulverized organic compound particles according to any one of (54) to (60), wherein the organic compound is a composition for medical use (for example, the poor water solubility organic compound for medical use) and is one or more organic compounds selected from the group consisting of an antipyretic drug, an analgesic drug, an anti-inflammatory drug, an antigout drug, a therapeutic drug for hyperuricemia, a sleeping medicine, a sedative drug, an anti-anxiety drug, an antipsychotic drug, an antidepressant, an antimanic drug, a psychostimulant, an antiepileptic drug, a muscle relaxant, a therapeutic drug for Parkinson's disease, a drug acting on the autonomic nerve system, a cerebral circulation and metabolism improving drug, a therapeutic drug for allergy, a cardiotonic drug, an antianginal drug, a β-blocker, a Ca-antagonist, an antiarrhythmic drug, an antidiuretic drug, a diuretic drug, a hypotensive drug, a therapeutic drug for peripheral circulation disorder, a drug for hyperlipidemia, a hypertensive drug, a respiratory stimulant, a bronchodilator, a therapeutic drug for asthma, an antitussive drug, an expectorant, a therapeutic drug for chronic obstructive pulmonary disease, a therapeutic drug for peptic ulcer, a purgative drug, an antidiarrheal/intestinal conditioner, a diabetic drug, an adrenal cortical hormone preparation, a sex hormone preparation, a drug for osteoporosis, a bone metabolism improving drug, a vitamin preparation, a hematinic drug, a blood coagulant preparation, a drug for chemotherapy, an antibiotic, an antifungal drug, an antiviral drug, an anticancer drug, an immunosuppressant, an ophthalmological drug, an otorhinolaryngological drug, a drug for oral cavity, a dermatological drug, a radiopharmaceutical, a diagnostic drug, a drug for life improvement, and a herbal medicine;

(62) A method for producing finely pulverized organic compound particles according to any one of (54) to (61), wherein the organic compound is one or more organic compounds selected from the group consisting of nifedipine, nicardipine, nimodipine, dipyridamole, disopyramide, prazosin hydrochloride, prednisolone, cortisone acetate, dexamethasone, betamethasone, beclometasone dipropionate, fluticasone propionate, budesonide, fluocinolone acetonide, indomethacin, naproxen, ketoprofen, 7-(3,5-dimethoxy-4-hydroxycinnamoylamino)-3-octyloxy-4-hydroxy-1-methyl-2(1H)-quinolinone, phenytoin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazone, phenprobamate, mequitazine, bisbentiamin, mitomycin C, bicalutamide, paclitaxel, ubenimex, dacarbazine, fluconazole, miconazole, rifampicin, triamcinolone acetonide, clemastine fumarate, pranlukast hydrate, zafirlukast and fenofibrate;

(63) A method for producing finely pulverized organic compound particles according to any one of (54) to (61), wherein the organic compound is one or more organic compounds selected from the group consisting of dihydroxybenzophenone, dihydrocholesterol, β-carotene, propyl gallate, cinnamic acid, saccharin, folic acid and maltol;

(63') A method for producing finely pulverized organic compound particles according to any one of (54) to (63), wherein the organic compound is an organic compound having a melting point of 120 degrees C. or more;

(64) A method for producing finely pulverized organic compound particles according to any one of (54) to (63'), wherein the salt is sodium chloride, and the polyol is glycerin;

(65) A method for producing finely pulverized organic compound particles according to any one of (54) to (64), wherein the wet-milling is carried out using one apparatus selected from the group consisting of a kneader, a twin-roll, a triple-roll, a fret mill and a disk blade kneader-disperser;

(66) Finely pulverized organic compound particles obtained by the method for producing finely pulverized organic compound particles according to any one of (54) to (65);

(67) A powder including the finely pulverized organic compound particles according to (66);

(68) An aqueous dispersion including the finely pulverized organic compound particles according to (66);

(69) An aqueous dispersion including the finely pulverized organic compound particles according to (66), and an additive for preventing secondary aggregation;

(70) A pharmaceutical composition including the finely pulverized organic compound particles according to (66), as an active ingredient; and

(71) A pharmaceutical composition, which is produced into porous particles having an average particle diameter of 1 to 30 μm, by suspending the poor water solubility organic compound fine particles for medical use according to (47) in water, and then carrying out a spray freeze-drying treatment.

The present invention also relates to the following aspect.

(72) Use of the poor water solubility organic compound fine particles for medical use according to any one of (1) to (21) and (47), for the production of a pharmaceutical composition; and

(73) Use of the finely pulverized organic compound particles according to (66), for the production of a pharmaceutical composition.

According to the present invention, the "average particle diameter" is the average particle diameter for an equivalent diameter such as the stokes diameter, the equivalent light scattering diameter, the diffusion equivalent diameter, the volume equivalent sphere diameter, the surface area equivalent sphere diameter, the area equivalent circle diameter, or the circumference equivalent circle diameter; preferably for the surface area equivalent sphere diameter or the equivalent light scattering diameter; and more preferably for the surface area equivalent sphere diameter. The surface area equivalent sphere diameter is, more specifically, a particle diameter measured by the BET method or the like. Preferably, the fine particle shape can be confirmed by using the observation under an electron microscope in combination. The equivalent light scattering diameter is, more specifically, a particle diameter measured by a laser diffraction light scattering method or a dynamic light scattering method. The average particle diameter (particularly, the average particle diameter measured by the BET method) of the poor water solubility organic compound powder for medical use of the present invention can be usually selected in the range of 600 nm or less, but the average particle diameter is preferably 500 nm or less, more preferably 450 nm or less, even more preferably 300 nm or less, still more preferably 200 nm or less, still more preferably 100 nm or less, and most preferably 80 nm or less. According to another embodiment, the average particle diameter (particularly, the average particle diameter measured by the BET method) of the poor water solubility organic compound powder for medical use of the present invention is preferably 10 nm or more, more preferably 20 nm or more, even more preferably 30 nm or more, still more preferably 40 nm or more, and most preferably 50 nm or more. The average particle diameter (particularly, the average particle diameter measured by the BET method) of the poor water solubility organic compound powder for medical use of the present invention is not particularly limited, but for example, the average particle diameter can be selected in the range of 10 nm or more and 600 nm or less, preferably 10 nm or more and 500 nm or less, more preferably 10 nm or more and 450 nm or less, even more preferably 10 nm or more and 300 nm or less, still more preferably 20 nm or more and 200 nm or less, still more preferably 30 nm or more and 100 nm or less, and most preferably 50 nm or more and 80 nm or less.

The fine particles of the present invention are preferably fine particles for which the ratio of particles having a diameter of 0.2 μm or less in the fine particles is 70% or more, or the 90% median diameter is 600 nm or less.

According to the present specification, the "90% median diameter" means the particle diameter at which, when the volume of the particles in a powder is integrated in order from the smaller particle diameter side, the cumulative volume becomes 90% of the total volume. This term may alternatively be referred to as "90% aggregate volume diameter" or "90% aggregate diameter". The 90% median diameter can be measured after conditioning the fine particles in a powder into an aqueous suspension using an optimal surface active agent, by dynamic light scattering or the like. The 90% median diameter of the fine particles of the present invention is preferably 500 nm or less, more preferably 400 nm or less, even more preferably 350 nm or less, still more preferably 300 nm or less, and most preferably 250 nm or less. In another aspect, the 90% median diameter of the fine particles of the present invention is preferably 50 nm or more, more preferably 70 nm or more, even more preferably 80 nm or more, still more preferably 90 nm or more, and most preferably 100 nm or more. The 90% median diameter of the fine particles of the present invention is preferably 50 nm to 500 nm, more preferably 70 nm to 400 nm, even more preferably 80 nm to 350 nm, still more preferably 90 nm to 300 nm, and most preferably 100 nm to 250 nm.

According to the present specification, the "ratio of particles having a diameter of 0.2 μm or less" is the ratio occupied by fine particles having a diameter of 0.2 μm or less in the total fine particles. The ratio of particles having a diameter of 0.2 μm or less may be the ratio based on the mass or may also be the ratio based on the volume, but is preferably the ratio based on the mass. For example, the ratio of particles having a diameter of 0.2 μm or less can be measured from the mass of the fine particles which have passed through a filter having a pore size of 0.2 μm. The ratio of the particles having a diameter of 0.2 μm or less in the fine particles of the present invention is preferably 70% or more, more preferably 80% or more, and even more preferably 90% or more. The upper limit of these ranges is not particularly limited and is 100%, but according to the present invention, the ratio of the particles having a diameter of 0.2 μm or less is usually in the range of 70% or more and 99% or less, and may be in the range of preferably 70% or more and 98% or less, more preferably 80% or more and 97% or less, and even more preferably 90% or more and 96% or less.

According to the present invention, being "poor water solubility" means that the solubility of an organic compound in water is low to the extent that the use as a pharmaceutical product is affected. The concept of poor water-solubility for pharmaceutical products can be referred to, for example, the descriptions of the pharmacopoeia of various countries. The solubility of a poor water solubility organic compound in water at the conventional temperature for handling organic compounds for medical use, for example, near room temperature 20° C., is about 10 mg/mL or less, preferably 1 mg/mL or less, more preferably 0.5 mg/mL or less, even more preferably 0.3 mg/mL or less, and most preferably 0.1 mg/mL or less. Here, the lower limit of the solubility in water is not particularly limited, but since in an example of very low solubility in water among those generally known poor water solubility compounds, the solubility is about $7 \times 10^{-15}$ mg/mL at 20° C., the solubility (20° C.) in water of the poor water solubility organic compound for medical use of the present invention can be in the range of $1 \times 10^{-30}$ mg/mL or more and 10 mg/mL or less, preferably $1 \times 10^{-30}$ mg/mL or more and 1 mg/mL or less, more preferably $1 \times 10^{-30}$ mg/mL or more and 0.5 mg/mL or less, even more preferably $1 \times 10^{-30}$ mg/mL or more and 0.3 mg/mL or less, and most preferably $1 \times 10^{-30}$ mg/mL or more and 0.1 mg/mL or less. A poor water solubility compound is, for example, a compound corresponding to "difficult to be dissolved", "extremely difficult to be dissolved" and "almost insoluble" according to the Japanese Pharmacopoeia, and preferably a compound corresponding to "extremely difficult to be dissolved" and "almost insoluble".

As for the "poor water solubility organic compound for medical use" according to the present invention, there may be mentioned, for example, the organic compounds can be adapted to an antipyretic drug, an analgesic drug, an anti-inflammatory drug, an antigout drug, a therapeutic drug for hyperuricemia, a sleeping medicine, a sedative drug, an antianxiety drug, an antipsychotic drug, an antidepressant, an antimanic drug, a psychostimulant, an antiepileptic drug, a muscle relaxant, a therapeutic drug for Parkinson's disease, a drug acting on the autonomic nerve system, a cerebral circulation and metabolism improving drug, a therapeutic drug for allergy, a cardiotonic drug, an antianginal drug, a β-blocker, a Ca-antagonist, an antiarrhythmic drug, an antidiuretic drug, a diuretic drug, a hypotensive drug, a therapeutic drug for peripheral circulation disorder, a drug for hyperlipidemia, a hypertensive drug, a respiratory stimulant, abronchodilator, a therapeutic drug for asthma, an antitussive drug, an expectorant, a therapeutic drug for chronic obstructive pulmonary disease, a therapeutic drug for peptic ulcer, a purgative drug, an antidiarrheal/intestinal conditioner, a diabetic drug, an adrenal cortical hormone preparation, a sex hormone preparation, a drug for osteoporosis, a bone metabolism improving drug, a vitamin preparation, a hematinic drug, a blood coagulant preparation, a drug for chemotherapy, an antibiotic, an antifungal drug, an antiviral drug, an anticancer drug, an immunosuppressant, an ophthalmological drug, an otorhinolaryngological drug, a drug for oral cavity, a dermatological drug, a radiopharmaceutical, a diagnostic drug, a drug for life improvement, and a herbal medicine.

In the case of simply referring to "organic compound" in the present invention, the compound includes the "poor water solubility organic compound for medical use", and the term "finely pulverized organic compound particles" includes the "poor water solubility organic compound fine particles for medical use".

The "poor water solubility organic compound for medical use" according to the present invention is preferably an organic compound having a melting point of 80 degrees C. or more. The melting point of the poor water solubility organic compound for medical use of the present invention is preferably 84 degrees C. or more, more preferably 120 degrees C. or more, even more preferably 150 degrees C. or more, and most preferably 200 degrees C. or more. Furthermore, the upper limit of the melting point of the "poor water solubility organic compound for medical use" according to the present invention is not particularly limited, but is preferably 350 degrees or less, and the melting point of the "poor water solubility organic compound for medical use" according to the present invention can be set in the range of preferably 84 degrees C. to 350 degrees C. or less, more preferably 120 degrees C. or more and 350 degrees C. or less, even more preferably 150 degrees C. or more and 350 degrees C. or less, and most preferably 200 degrees C. or more and 350 degrees C. or less.

The "poor water solubility organic compound for medical use" of the present invention is preferably a crystalline poor water solubility organic compound for medical use. According to the present specification, the "crystalline" is a state in which molecules are regularly aligned, and whether a certain substance is crystalline or not can be found by methods that are known to those having ordinary skill in the art, such as, for example, thermal analysis, X-ray diffraction and electron diffraction. Furthermore, the crystalline poor water solubility organic compound for medical use that is used in the method of the present invention, is preferably a hard organic compound having a dense crystal structure.

According to the present specification, the poor water solubility organic compound for medical use may be a naturally occurring substance, or may be a synthetic substance. Examples of the naturally occurring substance include animal-derived organic compounds, plant-derived organic compounds, organic compounds derived from microorganisms such as yeast, and the like. The poor water solubility organic compound for medical use of the present invention may be one species of organic compound, or may be two or more species of organic compounds.

Examples of such poor water solubility organic compounds for medical use include nifedipine, nicardipine, nimodipine, dipyridamole, disopyramide, prazosin hydrochloride, prednisolone, cortisone acetate, dexamethasone, betamethasone, beclometasone dipropionate, fluticasone propionate, budesonide, fluocinolone acetonide, indomethacin, naproxen, ketoprofen, 7-(3,5-dimethoxy-4-hydroxycinnamoylamino)-3-octyloxy-4-hydroxy-1-methyl-2(1H)-quinolinone, phenytoin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazone, phenprobamate, mequitazine, bisbentiamin, mitomycin C, bicalutamide, paclitaxel, ubenimex, dacarbazine, fluconazole, miconazole, rifampicin, triamcinolone acetonide, clemastine fumarate, pranlukast hydrate, zafirlukast, fenofibrate, dihydroxybenzophenone, dihydrocholesterol, β-carotene, propyl gallate, cinnamic acid, saccharin, folic acid and maltol. Preferable examples include indomethacin, nifedipine, cortisone acetate, β-carotene, beclometasone dipropionate, 7-(3,5-dimethoxy-4-hydroxycinnamoylamino)-3-octyloxy-4-hydroxy-1-methyl-2(1H)-quinolinone, miconazole, ketoprofen, fluticasone propionate, pranlukast hydrate, dexamethasone, zafirlukast and fenofibrate.

If the poor water solubility organic compound for medical use of the present invention is indomethacin, the average particle diameter of the fine particles of the present invention is preferably 240 nm or less, more preferably 180 nm or less, and even more preferably 156 nm or less. In another aspect, the average particle diameter of indomethacin fine particles is preferably 60 nm to 240 nm, more preferably 72 nm to 180 nm, and even more preferably 96 nm to 156 nm.

If the poor water solubility organic compound for medical use of the present invention is nifedipine, the average particle diameter of the fine particles of the present invention is preferably 500 nm or less, more preferably 390 nm or less, and even more preferably 338 nm or less. In another aspect, the average particle diameter of nifedipine fine particles is preferably 130 nm to 500 nm, more preferably 156 nm to 390 nm, and even more preferably 208 nm to 338 nm.

If the poor water solubility organic compound for medical use of the present invention is cortisone acetate, the average particle diameter of the fine particles of the present invention is preferably 500 nm or less, more preferably 390 nm or less, and even more preferably 338 nm or less. In another aspect, the average particle diameter of cortisone acetate is preferably 130 nm to 500 nm, more preferably 156 nm to 390 nm, and even more preferably 208 nm to 338 nm.

If the poor water solubility organic compound for medical use of the present invention is beclometasone dipropionate, the average particle diameter of the fine particles of the present invention is preferably 500 nm or less, more preferably 420 nm or less, and even more preferably 364 nm or less. In another aspect, the average particle diameter of beclametasone dipropionate fine particles is preferably 140 nm to 500 nm, more preferably 168 nm to 420 nm, and even more preferably 224 nm to 364 nm.

If the poor water solubility organic compound for medical use of the present invention is 7-(3,5-dimethoxy-4-hydroxycinnamoylamino)-3-octyloxy-4-hydroxy-1-methyl-2(1H)-quinolinone, the average particle diameter of the fine particles of the present invention is preferably 170 nm or less, more preferably 126 nm or less, and even more preferably 109 nm or less. In another embodiment, the average particle diameter of 7-(3,5-dimethoxy-4-hydroxycinnamoylamino)-3-octyloxy-4-hydroxy-1-methyl-2(1H)-quinolinone fine particles is preferably 42 nm to 170 nm, more preferably 50 nm to 126 nm, and even more preferably 67 nm to 109 nm.

If the poor water solubility organic compound for medical use of the present invention is miconazole, the average particle diameter of the fine particles of the present invention is preferably 500 nm or less, more preferably 441 nm or less, and even more preferably 382 nm or less. In another aspect, the average particle diameter of miconazole fine particles is preferably 147 nm to 500 nm, more preferably 176 nm to 441 nm, and even more preferably 235 nm to 382 nm.

If the poor water solubility organic compound for medical use of the present invention is ketoprofen, the average particle diameter of the fine particles of the present invention is preferably 500 nm or less, more preferably 369 nm or less, and even more preferably 170 nm or less. In another aspect, the average particle diameter of ketoprofen fine particles is preferably 142 nm to 500 nm, more preferably 170 nm to 426 nm, and even more preferably 227 nm to 369 nm.

If the poor water solubility organic compound for medical use of the present invention is fluticasone propionate, the average particle diameter of the fine particles of the present invention is preferably 300 nm or less, more preferably 220 nm or less, and even more preferably 200 nm or less. In another aspect, the average particle diameter of fluticasone propionate fine particles is preferably 50 nm to 300 nm, more preferably 60 nm to 220 nm, and even more preferably 70 nm to 200 nm.

If the poor water solubility organic compound for medical use of the present invention is pranlukast hydrate, the average particle diameter of the fine particles of the present invention is preferably 300 nm or less, more preferably 220 nm or less, and even more preferably 200 nm or less. In another aspect, the average particle diameter of pranlukast hydrate fine particles is preferably 50 nm to 300 nm, more preferably 60 nm to 220 nm, and even more preferably 70 nm to 200 nm.

If the poor water solubility organic compound for medical use of the present invention is dexamethasone, the average particle diameter of the fine particles of the present invention is preferably 300 nm or less, more preferably 220 nm or less, and even more preferably 200 nm or less. In another aspect, the average particle diameter of dexamethasone fine particles is preferably 50 nm to 300 nm, more preferably 60 nm to 220 nm, and even more preferably 70 nm to 200 nm.

If the poor water solubility organic compound for medical use of the present invention is zafirlukast, the average particle diameter of the fine particles of the present invention is preferably 298 nm or less, more preferably 222 nm or less, and even more preferably 192 nm or less. In another aspect, the average particle diameter of zafirlukast fine particles is preferably 74 nm to 298 nm, more preferably 88 nm to 222 nm, and even more preferably 118 nm to 192 nm.

If the poor water solubility organic compound for medical use of the present invention is fenofibrate, the average particle diameter of the fine particles of the present invention is preferably 500 nm or less, and more preferably 450 nm or less. In another aspect, the average particle diameter of fenofibrate fine particles is preferably 211 nm to 500 nm, more preferably 253 nm to 450 nm, and even more preferably 337 nm to 430 nm.

The fine particles of the present invention preferably do not substantially contain any material that is causative of contamination. The material that is causative of contamination may be a surface active agent, a metal, a resin, and the like. The term "not substantially contain" means the extent to which it is possible to use the fine particles for medical use, and can be appropriately determined by the uses of the fine particles of the present invention. The fine particles of the invention are preferably fine particles not containing a surface active agent.

According to the specification, the "composition for medical use" is not particularly limited as long as it is used for the purpose of treatment, prevention or diagnosis of human beings or animals. For example, the composition for medical use of the present invention may be administered into the body or the surface of a human being or an animal, or the blood, urine and the like collected from a human being or an animal may be treated extracorporeally. Examples of such a composition for medical use include an antipyretic drug, an analgesic drug, an anti-inflammatory drug, an antigout drug, a therapeutic drug for hyperuricemia, a sleeping medicine, a sedative drug, an anti-anxiety drug, an antipsychotic drug, an antidepressant, an antimanic drug, a psychostimulant, an antiepileptic drug, a muscle relaxant, a therapeutic drug for Parkinson's disease, a drug acting on the autonomic nerve system, a cerebral circulation and metabolism improving drug, a therapeutic drug for allergy, a cardiotonic drug, an antianginal drug, a β-blocker, a Ca-antagonist, an antiarrhythmic drug, an antidiuretic drug, a diuretic drug, a hypotensive drug, a therapeutic drug for peripheral circulation disorder, a drug for hyperlipidemia, a hypertensive drug, a respiratory stimulant, a bronchodilator, a therapeutic drug for asthma, an antitussive drug, an expectorant, a therapeutic drug for chronic obstructive pulmonary disease, a therapeutic drug for peptic ulcer, a purgative drug, an antidiarrheal/intestinal conditioner, a diabetic drug, an adrenal cortical hormone preparation, a sex hormone preparation, a drug for osteoporosis, a bone metabolism improving drug, a vitamin preparation, a hematinic drug, a blood coagulant preparation, a drug for chemotherapy, an antibiotic, an antifungal drug, an antiviral drug, an anticancer drug, an immunosuppressant, an ophthalmological drug, an otorhinolaryngological drug, a drug for oral cavity, a dermatological drug, a radiopharmaceutical, a diagnostic drug, a drug for life improvement, and a herbal medicine.

According to the present specification, the "porous fine particles" mean that they are fine particle assemblages formed into a spherical or irregular shape, and the fine particles of the present invention have pore-shaped voids are observed at the surface of the fine particle assemblages by an electron microscope. The porous fine particles of the present invention are not particularly limited as long as they are prepared using the fine particles of the present invention. It is preferable that the method for evaluating the porous fine particles is carried out by the measurement of specific surface area according to the BET method, the observation of particle surface by an electron microscope, and a particle size distribution analysis. Optionally, it is also possible to predict the presence of macropores (pores having a diameter of 50 nm or more), micropores (pores having a diameter of 2 nm or more), and mesopores (pores having a diameter of 2 to 50 nm), based on the adsorption-desorption isotherms in a gas adsorption method. Similarly, the pore distribution can also be measured. The porous fine particles are preferably such that the specific surface area measured by the BET method is preferably 3 $m^2/g$ or more, more preferably 5 $m^2/g$ or more, even more preferably 10 $m^2/g$ or more, still more preferably 15 $m^2/g$ or more, still more preferably 20 $m^2/g$ or more, and most preferably 30 $m^2/g$ or more. In another aspect, the specific surface area measured by the BET method of the porous fine particles of the present invention is preferably 300 $m^2/g$ or less, more preferably 200 $m^2/g$ or less, even more preferably 100 $m^2/g$ or less, still more preferably 90 $m^2/g$ or less, and most preferably 80 $m^2/g$ or less. The specific surface area measured by the BET method of the porous particles of the present invention is preferably 3 $m^2/g$ or more and 300 $m^2/g$ or less, more preferably 5 $m^2/g$ or more and 200 $m^2/g$ or less, even more preferably 10 $m^2/g$ or more and 100 $m^2/g$ or less, and most preferably 15 $m^2/g$ or more and 80 $m^2/g$ or less. The average particle diameter (average particle diameter analyzed by an electron microscope) of the porous fine particles of the present invention is preferably 0.5 to 50 μm, more preferably 0.8 to 30 μm, and most preferably 1 to 20 μm.

Effects of the Invention

The poor water solubility organic compound powder for medical use of the present invention can be stably suspended in an aqueous solvent because of its small particle size. The poor water solubility organic compound powder for medical use of the present invention can be efficiently absorbed into the living body or can have an increased bioavailability, because of the small particle size. In particular, since the poor water solubility organic compound powder for medical use of the present invention not only has a small particle size but also maintains a crystal form that offers the desired pharmaceutical effects, administration in a small amount to a patient can efficiently provide the drug efficacy. The production method of the present invention can process an organic compound for medical use into fine particles, even without using an impact grinding method and without using a solid pulverization aid such as beads made of glass, stainless steel, ceramics or a hard polymer, and therefore, the incorporation of abrasion powder or the like can be suppressed to the minimum. In regard to the salt and the polyol used in the pulverization, since physiologically acceptable salt and polyol are used, the components can be therefore used in the fine pulverization of an organic compound, which is a pharmaceutical composition.

The porous fine particles, which are assemblages of the poor water solubility organic compound powder for medical use of the present invention, have properties that are suitable as an inhalant, an injectable preparation or an oral preparation. For example, when the porous fine particles, which are assemblages of the poor water solubility organic compound powder for medical use of the present invention, are used as an inhalant, the particles can be sufficiently made to reach the throat, trachea, bronchus, lung sac and the like.

Furthermore, the method for producing poor water solubility organic compound particles for medical use of the present invention can produce very fine particles. Even after the process of fine pulverization, the crystal structure of the organic compound can be maintained. Therefore, the chemical stability of the organic compound is good, and there is a negligible risk of impairing the activity and the like that are inherently possessed by the organic compound. Since the method for producing poor water solubility organic compound particles for medical use of the present invention does not use surface active agents, the particles can be finely pulverized in a physiologically safe manner. The finely pulverized organic compound particles produced by the production method of the present invention can be used as a drug for medical use. Furthermore, since the finely pulverized organic compound particles of the present invention are particles having a very small average particle diameter, the absorbability into the body or the dispersibility in a solvent is good, and the suitability to processing such as formulation is also excellent.

The method for producing finely pulverized organic compound particles of the present invention can use existing pulverization apparatuses, and therefore, can be conveniently applied to industrial production. Moreover, since inexpensive salts and polyols are used, and expensive reagents or apparatuses are not needed, the method is also preferable in an economical viewpoint. For example, an organic compound which is soluble in a liquefied gas in the supercritical or near-critical state, can still be finely pulverized using a supercritical method, but mass production can be achieved by the method for producing finely pulverized organic compound particles of the present invention in a very economical manner. Furthermore, a target organic compound can be formed into very fine particles that have been traditionally unavailable, by the method for producing finely pulverized organic compound particles of the present invention. Also, by appropriately determining the type of the salt or polyol that is used in the pulverization, the conditions for wet-milling, and the like, not only fine particles can be formed, but also finely pulverized organic compound particles in the state of having a crystal structure can be produced. Accordingly, the resulting finely pulverized organic compound particles have excellent chemical stability, and can be expected to have high physiological activity, as compared to the fine particles produced by conventional fine pulverization methods.

Generally, pharmaceutical compositions that are less soluble in water often have poor bioabsorption properties. Thus, there are many organic compounds which exhibit excellent effects in the in vitro tests, but do not exhibit sufficient effects in the in vivo tests because of their low bioavailability. While such organic compounds are expected to exhibit excellent effects in the stage of development into pharmaceutical products, there occurs a problem that their development is often stopped. Since a target organic compound can be formed into finely pulverized organic compound particles having a small size that is traditionally unavailable, through the method for producing finely pulverized organic compound particles of the present invention, the bioabsorption properties of the organic compound are markedly improved, and thus efficient arrival to the target tissue, or a reduction in the amount of use of the medicament can be expected. Furthermore, since the particles are fine particles maintaining a crystal structure, development of preparations having excellent chemical stability or pharmacological activity is made possible. Application to formulations that have traditionally had difficulties in application, such as inhalants, injections and eye drops, is also made possible.

BRIEF DESCRIPTION OF THE DRAWINGS

FIG. 1A shows, in particular, the results for a quinolinone derivative before being finely pulverized.

FIG. 1B shows, in particular, the results for the quinolinone derivative obtained in Example 8.

FIG. 1C shows, in particular, the results for the quinolinone derivative obtained in Comparative Example 8.

DETAILED DESCRIPTION

Figure 1A:
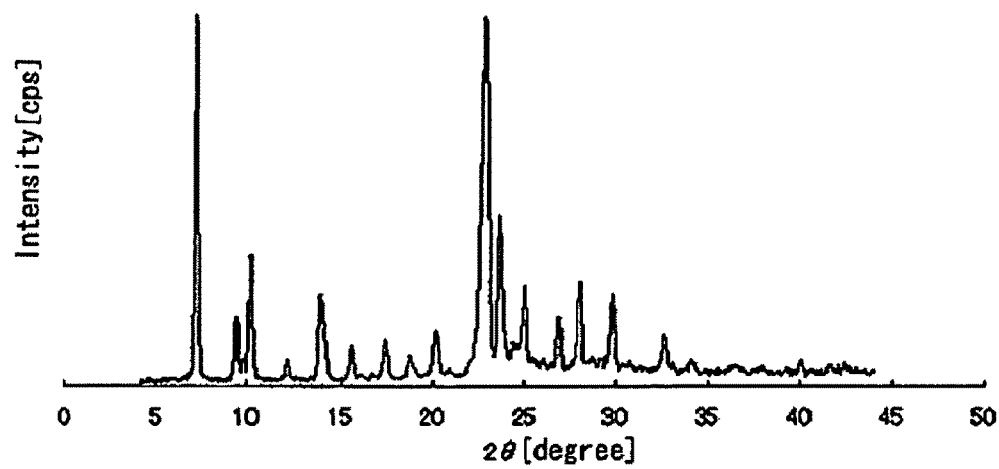
FIG. 1A is a diagram showing the results of X-ray diffraction obtained in Test Example 1, with the vertical axis representing the intensity, and the horizontal axis representing the diffraction angle.

Hereinafter, embodiments of the present invention will be described, with emphasis given to the poor water solubility organic compound fine particles for medical use and the method for producing organic compound fine particles for medical use of the present invention. Here, in regard to the method for producing finely pulverized organic compound particles of the present invention, and the finely pulverized organic compound particles obtained by the production method and the like, as previously described, the term "organic compound" according to the present invention is a superordinate concept including the "poor water solubility organic compound for medical use", and the term "finely pulverized organic compound particles" is also a superordinate concept including the "poor water solubility organic compound fine particles for medical use". In other words, the method for producing finely pulverized organic compound particles of the present invention, and the finely pulverized organic compound particles obtained thereby are not intended to be restricted particularly to medical uses, but include the uses as agrochemicals, food products and the like. Hereinafter, the embodiments of the poor water solubility organic compound fine particles for medical use or the method for producing organic compound fine particles for medical use as described in the following, can also be used in connection with the method for producing finely pulverized organic compound particles and the finely pulverized organic compound particles of the present invention.

The poor water solubility organic compound fine particles for medical use included in the powder of the present invention can be produced by mixing a poor water solubility organic compound for medical use with a physiologically acceptable salt and a physiologically acceptable polyol, and wet-milling the organic compound. Here, the mixing is considered satisfactory if the poor water solubility organic compound for medical use, the physiologically acceptable salt, and the physiologically acceptable polyol are finely mixed, and the order of addition of these components is not intended to be limited. For example, the mixing may be carried out by adding the physiologically acceptable salt and the physiologically acceptable polyol to the poor water solubility organic compound for medical use, or may also be carried out by adding the poor water solubility organic compound for medical use to the physiologically acceptable salt and the physiologically acceptable polyol. In particular, the poor water solubility organic compound fine particles for medical use that are included in the powder of the present invention can be produced by adding a physiologically acceptable salt and a physiologically acceptable polyol to an organic compound having a melting point of 80 degrees C. or more, wet-milling the organic compound, and then removing the salt and the polyol. The wet-milling can be carried out by mixing the organic compound, the salt and the polyol, and kneading the mixture.

Preferably, the poor water solubility organic compound fine particles for medical use of the present invention are produced by performing wet-milling without using a hard solid pulverization aid, and more preferably, the fine particles are produced by performing wet-milling without using a solid pulverization aid made of glass, of metal such as stainless steel, of ceramics such as zirconia and alumina, or of a polymer such as hard polystyrene. Most preferably, the poor water solubility organic compound fine particles for medical use of the present invention are produced by performing wet-milling, without using a solid pulverization aid.

As the poor water solubility organic compound for medical use that may be used for the production method of the present invention, an organic compound having a melting point of 80 degrees C. or more is used, but the organic compound is preferably an organic compound having a melting point of 84 degrees C. or more, more preferably an organic compound having a melting point of 120 degrees C. or more, even more preferably an organic compound having a melting point of 150 degrees C. or more, and most preferably an organic compound having a melting point of 200 degrees C. or more. In another aspect, the poor water solubility organic compound for medical use that may be used for the production method of the present invention is preferably an organic compound having a melting point of 350 degrees C. or less. The poor water solubility organic compound for medical use that may be used for the method of the present invention is preferably an organic compound having a dense and hard crystal structure, because an organic compound having a high melting point tends to have a hard crystal structure, and thus is suitable for the method for producing finely pulverized organic compound particles of the present invention.

In regard to the production method of the present invention, the poor water solubility organic compound for medical use that may be used for the method of the present invention to be wet-milled in polyol, is preferably an organic compound which is less soluble in polyol. The solubility of the poor water solubility organic compound for medical use in polyol is preferably 0.001 to 100% (mass/volume), more preferably 0.001 to 50% (mass/volume), and even more preferably 0.001 to 10% (mass/volume).

As for the poor water solubility organic compound for medical use that may be used for the production method of the present invention, there may be mentioned organic compounds that can be adapted to, for example, an antipyretic drug, an analgesic drug, an anti-inflammatory drug, an anti-gout drug, a therapeutic drug for hyperuricemia, a sleeping medicine, a sedative drug, an anti-anxiety drug, an antipsychotic drug, an antidepressant, an antimanic drug, a psychostimulant, an antiepileptic drug, a muscle relaxant, a therapeutic drug for Parkinson's disease, a drug acting on the autonomic nerve system, a cerebral circulation and metabolism improving drug, a therapeutic drug for allergy, a cardiotonic drug, an antianginal drug, a β-blocker, a Ca-antagonist, an antiarrhythmic drug, an antidiuretic drug, a diuretic drug, a hypotensive drug, a therapeutic drug for peripheral circulation disorder, a drug for hyperlipidemia, a hypertensive drug, a respiratory stimulant, a bronchodilator, a therapeutic drug for asthma, a therapeutic drug for chronic obstructive pulmonary disease, an antitussive drug, an expectorant, a therapeutic drug for peptic ulcer, a purgative drug, an antidiarrheal/intestinal conditioner, a diabetic drug, an adrenal cortical hormone preparation, a sex hormone preparation, a drug for osteoporosis, a bone metabolism improving drug, a vitamin preparation, a hematinic drug, a blood coagulant preparation, a drug for chemotherapy, an antibiotic, an antifungal drug, an antiviral drug, an anticancer drug, an immunosuppressant, an ophthalmological drug, an otorhinolaryngological drug, a drug for oral cavity, a dermatological drug, a radiopharmaceutical, a diagnostic drug, a drug for life improvement, and a herbal medicine.

Examples of the poor water solubility organic compound for medical use that may be used for the production method of the present invention include nifedipine (melting point: 172 to 175 degrees C.), nicardipine (melting point: 136 to 138 degrees C.), nimodipine (melting point: 123 to 126 degrees C.), dipyridamole (melting point: 165 to 169 degrees C.), disopyramide (melting point: about 204 degrees C.), prazosin hydrochloride (melting point: about 275 degrees C. (decomposed)), prednisolone (melting point: about 235 degrees C. (decomposed)), cortisone acetate (melting point: about 240 degrees C. (decomposed)), dexamethasone (melting point: about 245 degrees C. (decomposed)), betamethasone (melting point: about 240 degrees C. (decomposed)), beclometasone dipropionate (melting point: about 208 degrees C. (decomposed)), fluticasone propionate (melting point: about 273 degrees C. (decomposed)), budesonide (melting point: about 240 degrees C. (decomposed)), fluocinolone acetonide (melting point: about 266 to 274 degrees C. (decomposed)), indomethacin (melting point: 155 to 162 degrees C.), naproxen melting point: 154 to 158 degrees C.), ketoprofen (melting point: 94 to 97 degrees C.), 7-(3,5-dimethoxy-4-hydroxycinnamoylamino)-3-octyloxy-4-hydroxy-1-methyl-2(1H)-quinolinone (hereinafter, referred to as quinolinone derivative) (melting point: 186 to 187 degrees C.), phenytoin (melting point: about 296 degrees C. (decomposed)), phenacemide (melting point: 214 to 216 degrees C.), ethotoin (melting point: 90 to 95 degrees C.), primidone (melting point: 279 to 284 degrees C.), diazepam (melting point: 130 to 134 degrees C.), nitrazepam (melting point: about 227 degrees C. (decomposed)), clonazepam (melting point: about 240 degrees C. (decomposed)), digitoxin (melting point: 256 to 257 degrees C. (decomposed)), spironolactone (melting point: 198 to 207 degrees C.), triamterene (melting point: 316 degrees C.), chlorthalidone (melting point: 217 degrees C.), polythiazide (melting point: 202.5 degrees C.), benzthiazide (melting point: 231.5 degrees C.), griseofulvin (melting point: 218 to 222 degrees C.), nalidixic acid (melting point: 225 to 231 degrees C.), chloramphenicol (melting point: 149 to 153 degrees C.), chlorzoxazone (melting point: 188 to 192 degrees C.), phenprobamate (melting point: 102 to 105.5 degrees C.), mequitazine (melting point: 146 to 150 degrees C.), bisbentiamin (melting point: 140 to 144 degrees C.), triamcinolone acetonide (melting point: about 290 degrees C. (decomposed) ), fluconazole (melting point: 137 to 141 degrees C.), miconazole (melting point: 84 to 87 degrees C.), rifampicin (melting point: 183 to 188 degrees C. (decomposed)), dacarbazine (melting point: about 204 degrees C. (decomposed)), mitomycin C (melting point: 300 degrees C. or more), bicalutamide (melting point: 190 to 195 degrees C.), paclitaxel (melting point: 220 to 223 degrees C.), ubenimex (melting point: about 234 degrees C. (decomposed)), clemastine fumarate (melting point: 176 to 180 degrees C. (decomposed)), erythronycin (melting point: 133 to 138 degrees C.), amphotericin B (melting point: 170 degrees C.), cefixime (melting point: about 240 degrees C. (decomposed)), salazosulfapyridine (melting point: 240 to 249 degrees C.), sparfloxacin (melting point: 266 degrees C. (decomposed)), tinidazole (melting point: 125 to 129 degrees C.), vidarabine (melting point: 248 to 254 degrees C. (decomposed)), aciclovir (melting point: 300 degrees C. (decomposed)), milrinone (melting point: about 317 degrees C. (decomposed)), digoxin (melting point: about 230 to 265 degrees C. (decomposed)), pindolol (melting point: 169 to 173 degrees C.), propafenone hydrochloride (melting point: 172 to 175 degrees C.), amrinone (melting point: about 297 degrees C. (decomposed)), hydrochlorothiazide (melting point: 263 to 270 degrees C. (decomposed)), trandolapril (melting point: 123 to 126 degrees C.), candesartan cilexetil (melting point: 163.6 to 164.1 degrees C. (decomposed)), urapidil (melting point: 156 to 161 degrees C.), reserpine (melting point: 264 to 265 degrees C. (decomposed)), methyldopa (melting point: 295 to 298 degrees C. (decomposed)), norepinephrine (melting point: about 191 degrees C. (decomposed)), simvastatin (melting point: 135 to 138 degrees C.), fluoxymesterone (melting point: 270 to 278 degrees C.), stanozolol (melting point: 230 to 242 degrees C.), estradiol (melting point: 175 to 180 degrees C.), chlormadinone acetate (melting point: 211 to 215 degrees C.), falecalcitriol (melting point: about 143 degrees C.), mazindol (melting point: about 177 to 184 degrees C. (decomposed)), sildenafil citrate (melting point: about 200 to 201 degrees C.), minoxidil (melting point: 248 degrees C.), droperidol (melting point: about 145 to 149 degrees C.), quazepam (melting point: 148 to 151 degrees C.), pentazocine (melting point: 154 degrees C.), propericiazine (melting point: 113 to 118 degrees C.), timiperone (melting point: 200 to 203 degrees C.), sulpiride (melting point: 175 to 182 degrees C. (decomposed)), amoxapine (melting point: 178 to 182 degrees C. (decomposed)), lisuride maleate (melting point: about 195 degrees C. (decomposed)), nicergoline (melting point: 134 to 138 degrees C. (decomposed)), biperiden (melting point: 112 to 115 degrees C.), levodopa (melting point: about 275 degrees C. (decomposed)), chlorphenesin carbamate (melting point: 88 to 91 degrees C.), dantrolene sodium (melting point: 200 degrees C. or more (decomposed)), formoterol fumarate (melting point: about 138 degrees C. (decomposed)), atenolol (melting point; 153 to 156 degrees C.), riluzole (melting point: about 118 degrees C.), flumazenil (melting point: 198 to 202 degrees C.), theophylline (melting point: 271 to 275 degrees C. (decomposed)), methotrexate (melting point: 185 to 204 degrees C. (decomposed)), amidotrizoic acid (melting point: 291 to 308 degrees C. (decomposed) ), cilostazol (melting point: 158 to 162 degrees C.), adenine (melting point: about 360 degrees C. (decomposed)), tolbutamide (melting point: 126 to 132 degrees C.), famotidine (melting point: about 164 degrees C. (decomposed)), ursodesoxycholic acid (melting point: 200 to 204 degrees C.), sulindac (melting point: 180 to 187 degrees C.), pirenoxine (melting point: about 245 degrees C. (decomposed)), flunisolide (melting point: about 243 degrees C. (decomposed)), danazol (melting point: 223 to 227 degrees C. (decomposed)), tacrolimus hydrate (melting point: about 130 to 133 degrees C.), β-carotene (melting point: 176 to 183 degrees C.), pranlukast hydrate (melting point: 231 to 235 degrees C. (decomposed)), zafirlukast (melting point: about 200 degrees C. (decomposed)), and fenofibrate (melting point: 80 to 83 degrees C.). For these organic compounds, those compounds produced by previously known methods can be used.

According to the present specification, the term "physiologically acceptable" means that the substance can be taken in without causing any particular physiological problem. Whether a substance is a physiologically acceptable substance or not is appropriately determined by the subject organism of intake, the form of intake, or the like. Examples of physiologically acceptable solvents include the materials approved as the additives or solvents for pharmaceutical products or food products, and the like.

The "physiologically acceptable salt" that may be used for the production method of the present invention is not particularly limited, as long as it is a salt that can be taken in without causing any particular physiological problem. Preferred examples of the physiologically acceptable salt include salts that are less soluble in polyols, salts that are highly soluble in water, and/or salts that are less hygroscopic and have a hardness suitable for the fine pulverization of organic compounds. More preferred as the physiologically acceptable salt that may be used for the production method of the present invention, is a salt having two or more of these properties. The solubility of the physiologically acceptable salt in polyol is preferably 10% (mass/volume) or less. Furthermore, in the case of performing the removal after pulverization more conveniently, the physiologically acceptable salt is preferably a salt having high solubility in water.

Examples of the "physiologically acceptable salt" that may be used for the production method of the present invention include sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate and dipotassium hydrogen phosphate. Sodium chloride, potassium chloride, magnesium sulfate, calcium sulfate, sodium citrate, sodium dihydrogen phosphate, potassium dihydrogen phosphate, disodium hydrogen phosphate, dipotassium hydrogen phosphate, and the like may be mentioned, and preferred is sodium chloride.

The "physiologically acceptable salt" that may be used for the production method of the present invention is preferably subjected to pulverization or the like, prior to mixing with the poor water solubility organic compound for medical use, so as to adjust the particle diameter. As necessary, the physiologically acceptable salt may also be treated to lower the moisture ratio by, for example, drying under reduced pressure at a temperature of 30 to 200 degrees C., for the purpose of preventing particle fusion and particle growth due to the moisture contained therein. In the case of adjusting the particle diameter of the physiologically acceptable salt in advance, the volume average diameter of the particle may be, for example, 5 to 300 µm, or 10 to 200 µm, but the volume average diameter is preferably 0.01 to 300 µm, more preferably 0.1 to 100 µm, even more preferably 0.5 to 50 µm, and most preferably 1 to 5 µm. The amount of use of the salt is preferably 1- to 100-fold, more preferably 5- to 30-fold, and even more preferably 10- to 20-fold, with respect to the mass of the poor water solubility organic compound for medical use. The salts may be used individually, or may be used as mixtures of two or more species.

The "physiologically acceptable polyol" that may be used for the production method of the present invention is not particularly limited, as long as it is a polyol that can be taken in without causing any particular physiological problem. Preferred examples of the physiologically acceptable polyol include polyols having low solubility for salts, polyols that are highly soluble in water, polyols having low freezing point, and/or polyols having high flash point. In the case of performing the removal after pulverization more conveniently, the physiologically acceptable polyol is preferably a polyol having high solubility in water.

Examples of the "physiologically acceptable polyol" that may be used for the production method of the present invention include glycerin, propylene glycol, polyethylene glycol, dipropylene glycol, and diethylene glycol, and preferred is propylene glycol or glycerin. The polyol that is used for the production method of the present invention is preferably a polyol having high viscosity. The viscosity of such a polyol at 20 degrees C. is, for example, 40 mPa·s or more, preferably 50 mPa·s or more, and more preferably 80 mPa·s or more. The upper limit of the viscosity at 20 degrees C. of the polyol that is used for the production method of the present invention is not particularly limited, but can be selected in the range of, for example, 40 mPa·s or more and 5,000 mPa·s or less, preferably 50 mPa·s or more and 3,000 mPa·s or less, and more preferably 80 mPa·s or more and 2,000 mPa·s or less.

The amount of use of the physiologically acceptable polyol in the production method of the present invention is preferably 1- to 100-fold, and more preferably 2- to 10-fold, with respect to the mass of the organic compound that is to be finely pulverized. The type of the polyol used can be appropriately determined while taking into consideration of the solubility of the organic compound that is to be finely pulverized. The polyols may be used individually, or may be used as mixtures of two or more species.

In regard to the production method of the present invention, it is preferable that the kneading product of the poor water solubility organic compound for medical use, the polyol and the salt, have a high viscosity. As for the method of increasing the viscosity of the kneading product, a method of using a mixture prepared by adding a viscosity modifier to the polyol is preferable and can effectively increase the pulverization efficiency. The viscosity modifier that is to be added to the polyol is preferably a physiologically acceptable compound having an effect of increasing the viscosity when dissolved or suspended in the polyol. In the case of performing the removal after pulverization more conveniently, the viscosity modifier preferably has high solubility in water, and examples include citric acid, DL-malic acid, D-sorbitol, D-mannitol, maltitol, maltose, tartaric acid, glucose, erythritol, xylitol, D-xylose, trehalose, fructose, lactic acid, lactose, glycine, urea, maleic acid and malonic acid, while citric acid is preferred. The viscosity at 20 degrees C. of the polyol added with such a viscosity modifier is preferably 1,000 mPa·s or more, more preferably 2,000 mPa·s or more, even more preferably 5,000 mPa·s or more, and most preferably 10,000 mPa·s or more. The upper limit of the viscosity at 20 degrees C. of the polyol added with a viscosity modifier of the present invention is not particularly limited, but can be selected in the range of, for example, 1,000 mPa·s or more and 5,000,000 mPa·s or less, preferably 1,000 mPa·s or more and 1,000,000 mPa·s or less, more preferably 2,000 mPa·s or more and 500,000 mPa·s or less, even more preferably 5,000 mPa·s or more and 300,000 mPa·s or less, and most preferably 10,000 mPa·s or more and 100,000 mPa·s or less.

In regard to the pulverization apparatus used to perform wet-milling of the poor water solubility organic compound for medical use according to the production method of the present invention, any apparatus can be used without particular limitation, as long as the apparatus is capable of kneading and dispersion of the poor water solubility organic compound for medical use, salt, polyol and/or viscosity modifier by a mechanical means. Examples of the pulverization apparatus include those conventionally used pulverization apparatuses such as a kneader, a twin-roll, a triple-roll, a fret mill, a Hoover muller, and a disk blade kneader-disperser.

The pulverization temperature can be appropriately determined while taking into consideration of the poor water solubility organic compound for medical use that is to be finely pulverized, the pulverization apparatus, or the like. The pulverization temperature is not particularly limited, but is preferably −50 to 50 degrees C., more preferably −20 to 30 degrees C., and most preferably −10 to 25 degrees C. The pulverization time can be appropriately determined while taking into consideration of the organic compound that is to be finely pulverized, the pulverization apparatus, or the like. The pulverization time may be, for example, about 1 to 50 hours, preferably 3 to 30 hours, more preferably 5 to 20 hours, and most preferably 6 to 18 hours.

After completion of the pulverization of the poor water solubility organic compound for medical use, the salt and polyol used in the pulverization are removed, and thereby the desired finely pulverized poor water solubility organic compound fine particles for medical use can be obtained. Specifically, the mixture of the poor water solubility organic compound for medical use, salt, polyol and/or viscosity modifier is made uniform in a solvent using a homogenizer or the like, and then the salt, polyol and/or viscosity modifier are removed by filtration and washing with water. The solvent that maybe used for making the mixture uniform, is a solvent in which the polyol, the salt and the viscosity modifier are easily dissolved, while the finely pulverized poor water solubility organic compound for medical use is difficult to be dissolved. The solvent is not particularly limited as long as it is a physiologically acceptable solvent. The solvent is preferably water, but solvents other than water can also be used. Examples of the solvents other than water include mixed liquids of organic solvents such as acetic acid, methanol and ethanol, with water. The method of filtration is not particularly limited, and can be usually carried out by a known method that is used for filtering the contents of organic compounds. Examples of the filtration method include a vacuum filtration method, a pressure filtration method, an ultrafiltration membrane method, and the like.

Finely pulverized particles are likely to aggregate because they usually have high surface energy. Thus, an additive for preventing secondary aggregation may be added after removing the salt and the like. Examples of the secondary aggregation preventing agent include ethanol, glycerin, propylene glycol, sodium citrate, purified soybean lecithin, phospholipids, D-sorbitol, lactose, xylitol, gum arabic, sucrose fatty acid esters, polyoxyethylene hydrogenated castor oil, polyoxyethylene fatty acid esters, polyoxyethylene glycol, polyoxyethylene sorbitan fatty acid esters, alkylsulfuric acid salts, alkylbenzenesulfonic acid salts, sulfosuccinic acid ester salts, polyoxyethylene polyoxypropylene glycol, polyvinylpyrrolidone, polyvinyl alcohol, hydroxypropylcellulose, methylcellulose, hydroxyethylcellulose, hydroxypropylmethylcellulose, carmellose sodium, carboxymethyl polymers, N-acylglutamic acid salts, acrylic acid copolymers, methacrylic acid copolymers, casein sodium, L-valine, L-leucine, L-isoleucine, benzalkonium chloride, benzethonium chloride, and the like. The secondary aggregation preventing agent may be used individually, or may be used as mixtures of two or more species of secondary aggregation preventing agents.

After removing the salt and the polyol, the solvent used in the removal of the salt or the like can be removed from the obtained finely pulverized poor water solubility organic compound fine particles for medical use, by performing a drying treatment. The drying method is not particularly limited, and a method that is usually used to dry an organic compound can be carried out. Examples of the drying method include a vacuum drying method, a freeze-drying method, a spray drying method, a freeze-spray drying method, and the like. The drying temperature or drying time for the process of drying are not particularly limited, but it is preferable to perform the drying at low temperature for the purpose of maintaining the chemical stability of the organic compound particles for medical use and preventing secondary aggregation of the particles, and it is preferably to perform a freeze-drying method, a spray drying method, or a freeze-spray drying method.

The average particle diameter of the finely pulverized poor water solubility organic compound fine particles for medical use obtained by the production method of the present invention, is usually in the range of 600 nm or less. The average particle diameter may depend on the type of the organic compound used, the conditions of production, or the like, but can be in the range of, for example, 10 to 500 nm, 20 to 300 nm, or 20 to 200 nm. The average particle diameter of the finely pulverized poor water solubility organic compound fine particles of medical use obtained by the production method of the present invention is preferably in the range of 500 nm or less, more preferably 450 nm or less, even more preferably 300 nm or less, still more preferably 200 nm or less, still more preferably 100 nm or less, and most preferably 80 nm or less. In another aspect, the average particle diameter of the finely pulverized poor water solubility organic compound fine particles for medical use obtained by the production method of the present invention is preferably in the range of 10 nm or more, more preferably 20 nm or more, even more preferably 30 nm or more, still more preferably 40 nm or more, and most preferably 50 nm or more. The range of the average particle diameter of the finely pulverized poor water solubility organic compound fine particles for medical use obtained by the production method of the present invention is not particularly limited, but the average particle diameter can be selected in the range of, for example, 10 nm or more and 600 nm or less, preferably 10 nm or more and 500 nm or less, more preferably 10 nm or more and 450 nm or less, even more preferably 10 nm or more and 300 nm or less, still more preferably 20 nm or more and 200 nm or less, still more preferably 30 nm or more and 100 nm or less, and most preferably 50 nm or more and 80 nm or less. The average particle diameter of the particles can be measured by conventionally used particle size measurement techniques such as a microscopic method, a screening method, a Coulter counter method, a sedimentation method, an air permeation method, and a gas adsorption method, but the average particle diameter according to the present invention means the average particle diameter measured according to a gas adsorption method. The method is based on the principle that when molecules or ions having a known size are adsorbed to the surface of the particles, the particles adsorb the molecules or ion according to the specific surface area. Thus, the method is a method of determining the specific surface area using an adsorption isotherm equation or an isotherm, and calculating the average particle diameter, and the method is excellent as a method for measuring the average particle diameter of finely pulverized particles.

The poor water solubility organic compound fine particles for medical use of the present invention have excellent characteristics as preparations, and thus can be used as pharmaceutical products of various formulations.

For example, in the case of using the fine particles as an inhalant, a solvent-containing solid matter (hereinafter, referred to as wet cake) of the finely pulverized poor water solubility organic compound fine particles for medical use obtained by removing the salt and polyol after pulverization, is suspended in water, and can be prepared into porous particles having a size of about 1 to 30 μm by a freeze-spray drying method. A small amount of a surface active agent may also be added to water, in order to improve the dispersibility of the particles. Similarly, in order to improve the dispersibility, a small amount of a volatile additive such as ethanol may also be added. When a volatile additive is added, ethanol can be distilled off during the process of drying, and therefore, irritancy can be remedied in comparison to the case of adding a surface active agent. The spherical or irregularly shaped porous particles having a size of about 1 to 30 μm thus obtained, have a light specific weight because of their porousness, and also have satisfactory fluidity. Thus, the particles have excellent characteristics as an inhalant.

In the case of using the poor water solubility organic compound fine particles for medical use of the present invention in an injectable preparation, an eye drop, an ointment, a transdermal absorption preparation or the like, an aqueous dispersion can be prepared by adding a secondary aggregation preventing agent to the wet cake, and used. As the secondary aggregation preventing agent, for example, known surface active agents, and the like may be mentioned. Specifically, use can be made of the compounds mentioned as the secondary aggregation preventing agent that can be added after removing the salt or the polyol. An aqueous dispersion prepared by using a polymer such as an acrylic acid copolymer or a methacrylic acid copolymer as the secondary aggregation preventing agent, can be used as a DDS preparation. At the time of preparing an aqueous dispersion, the apparatuses that are conventionally used may be used. Examples of such apparatuses include a homogenizer, a homomixer, an ultrasonic disperser, a high pressure homogenizer, and the like.

The aqueous dispersion can also be formed into a powder by spray drying, freeze-drying, freeze-spray drying or the like. The powder thus produced has excellent redispersibility in water, and therefore, has excellent characteristics as an injectable preparation that is extemporaneously prepared at the time of use, an eye drop, or an oral preparation.

The finely pulverized poor water solubility organic compound fine particles for medical use of the present invention can also be dispersed in an oily substance and used as an ointment, a capsule preparation, a transdermal absorption preparation, or the like. The oily substance is not particularly limited as long as it is a substance that can be used in the conventional processes of formulation. Examples of the oily substance include liquid paraffin, petrolatum, propylene glycol, glycerin, polyethylene glycol, plant oil, and the like. The oily substances may be used individually, or may be used as mixtures of two or more oily substances. At the time of preparing a dispersion in an oily substance, the apparatuses that are conventionally used may be used. Examples of such apparatuses include a homogenizer, a homomixer, an ultrasonic disperser, a high pressure homogenizer, a twin-roll, a triple-roll, a disk blade kneader-disperser, and the like.

Next, the present invention will be described in more detail by way of Examples, but the present invention is not intended to be limited to the following Examples. The measurement of the average particle size was all carried out using a BET type specific surface area analyzer (Macsorb type MH-1201, manufactured by Mountech Co., Ltd.).

1. Pulverization of Various Organic Compounds for Medical Use According to Method of Present Invention As the organic compound for medical use, indomethacin, nifedipine, cortisone acetate, β-carotene, fenofibrate, beclometasone dipropionate, the quinolinone derivative [7-(3,5-dimethoxy-4-hydroxycinnamoylamino)-3-octyloxy-4-hydroxy-1-methyl-2 (1H)-quinolinone], miconazole, ketoprofen, fluticasone propionate, pranlukast hydrate, dexamethasone, and zafirlukast were used to be finely pulverized by the method of the present invention and a method of using a jet mill.

Example 1

9.3 g of indomethacin (melting point: 155 to 162 degrees C.) having an average particle diameter of 3,980 nm, and 140.7 g of pulverized sodium chloride (average particle diameter 5 μm) were introduced into a 0.2-L kneader (destructive type kneader, manufactured by Yoshida Seisakusho Co., Ltd.), and were mixed uniformly. Then, 35.5 g of glycerin was gradually injected therein, the content was kneaded and maintained in a dough form, and pulverization was carried out for 15 hours at 5 degrees C. Subsequently, the content was placed in 1 L of a 0.1 mol/L aqueous solution of acetic acid, and the mixture was uniformly dispersed with a homogenizer. The dispersion was then filtered and washed with water, and the resulting wet cake was dried under reduced pressure at 40 degrees C., to obtain 8.7 g of indomethacin having an average particle diameter of 120 nm.

Comparative Example 1

Pulverization of indomethacin was performed using a jet mill (Type 50-AS, manufactured by Hosokawa Alpine AG), at a supply air pressure of 0.5 MPa and a milling air pressure of 0.3 MPa. The average particle diameter of the resulting indomethacin was 1,060 nm.

Example 2

13.6 g of nifedipine (melting point: 172 to 175 degrees C.) having an average particle diameter of 4,310 nm, and 136.4 g of pulverized sodium chloride (average particle diameter 5 μm) were introduced into a 0.2-L kneader, and were mixed uniformly. Then, 28 g of glycerin was gradually injected therein, the content was kneaded and maintained in a dough form, and pulverization was carried out for 8 hours at 10 degrees C. Subsequently, the content was placed in 1 L of a 0.1 mol/L aqueous solution of acetic acid, and the mixture was uniformly dispersed with a homogenizer. The dispersion was then filtered and washed with water, and the resulting wet cake was dried under reduced pressure at 50 degrees C., to obtain 9.8 g of nifedipine having an average particle diameter of 260 nm.

Comparative Example 2

Pulverization of nifedipine was performed in the same manner as in Comparative Example 1. The average particle diameter of the resulting nifedipine was 910 nm.

Example 3

9.0 g of cortisone acetate (melting point: about 240 degrees C.) having an average particle diameter of 1,060 nm, and 141 g of pulverized sodium chloride (average particle diameter 5 μm) were introduced into a 0.2-L kneader, and were mixed uniformly. Then, 38 g of glycerin was gradually injected therein, the content was kneaded and maintained in a dough form, and pulverization was carried out for 18 hours at 10 degrees C. Subsequently, the content was placed in 1 L of a 0.1 mol/L aqueous solution of acetic acid, and the mixture was uniformly dispersed with a homogenizer. The dispersion was then filtered and washed with water, and the resulting wet cake was dried under reduced pressure at 50 degrees C., to obtain 7.4 g of cortisone acetate having an average particle diameter of 260 nm.

Example 4

9.0 g of β-carotene (melting point: 176 to 183 degrees C.) having an average particle diameter of 1,720 nm, and 141 g of pulverized sodium chloride (average particle diameter 5 μm) were introduced into a 0.2-L kneader, and were mixed uniformly. Then, 42 g of glycerin was gradually injected therein, the content was kneaded and maintained in a dough form, and pulverization was carried out for 6 hours at −4 degrees C. Subsequently, the content was placed in 1 L of distilled water, and the mixture was uniformly dispersed with a homogenizer. The dispersion was then filtered and washed with water, and the resulting wet cake was dried under reduced pressure at 50 degrees C., to obtain 7.5 g of β-carotene having an average particle diameter of 200 nm.

Comparative Example 3

Pulverization of β-carotene was performed in the same manner as in Comparative Example 1. The average particle diameter of the resulting β-carotene was 570 nm.

Example 5

0.1 g of fenofibrate (melting point: 80 to 83 degrees C.) having an average particle diameter of 6,640 nm, and 2.2 g of pulverized sodium chloride (average particle diameter 5 μm) were introduced into a water-cooling type Hoover muller, and were mixed uniformly. Then, 0.56 g of a viscous liquid of glycerin containing 50% by weight of citric acid (viscosity: 20 degrees C., 70,000 mPa·s) was slowly added dropwise, the content was kneaded and maintained in a dough form, and pulverization was carried out by kneading 100 cycles at 20 degrees C. Subsequently, the content was placed in 50 mL of a 0.1 mol/L aqueous solution of acetic acid, and the mixture was uniformly dispersed with an ultrasonic apparatus (TU-105, manufactured by Sharp Manufacturing System Corporation). The dispersion was then filtered and washed with water, and the resulting wet cake was redispersed by the ultrasonic apparatus and then freeze-dried, to obtain 0.075 g of fenofibrate having an average particle diameter of 423 nm.

Comparative Example 4

Pulverization of fenofibrate was performed in the same manner as in Comparative Example 1. The average particle diameter of the resulting fenofibrate was 1,377 nm.

Example 6

8.0 g of beclometasone dipropionate (melting point: about 208 degrees C.) having an average particle diameter of 1,820 nm, and 134 g of pulverized sodium chloride (average particle diameter 5 μm) were introduced into a 0.2-L kneader, and were mixed uniformly. Then, 30 g of glycerin was gradually injected therein, the content was kneaded and maintained in a dough form, and pulverization was carried out for 8 hours at 10 degrees C. Subsequently, the content was placed in 500 mL of a 0.1 mol/L aqueous solution of acetic acid, and the mixture was uniformly dispersed with a homogenizer. The dispersion was then filtered and washed with water, and the resulting wet cake was dried under reduced pressure at 50 degrees C., to obtain 7.1 g of beclometasone dipropionate having an average particle diameter of 280 nm.

Comparative Example 5

Pulverization of beclometasone dipropionate was performed in the same manner as in Comparative Example 1. The average particle diameter of the resulting beclometasone dipropionate was 730 nm.

Example 7

13.6 g of the quinolinone derivative [7-(3,5-dimethoxy-4-hydroxycinnamoylamino)-3-octyloxy-4-hydroxy-1-methyl-2(1H)-quinolinone] (melting point: 186 to 187 degrees C.) having an average particle diameter of 1,280 nm, and 136.4 g of pulverized sodium citrate were introduced into a 0.2-L kneader, and were mixed uniformly. Then, 28 g of propylene glycol was gradually injected therein, the content was kneaded and maintained in a dough form, and pulverization was carried out for 15.5 hours at 5 degrees C. in an argon gas atmosphere. Subsequently, the content was placed in 1 L of a 0.1 mol/L aqueous solution of acetic acid, and the mixture was uniformly dispersed with a homogenizer. The dispersion was then filtered and washed with water, and the resulting wet cake was dried under reduced pressure at 40 degrees C., to obtain 11.8 g of the quinolinone derivative having an average particle diameter of 130 nm.

Example 8

13.6 g of the quinolinone derivative [7-(3,5-dimethoxy-4-hydroxycinnamoylamino)-3-octyloxy-4-hydroxy-1-methyl-2(1H)-quinolinone] having an average particle diameter of 1,280 nm, and 136.4 g of pulverized sodium chloride (average particle diameter 5 μm) were introduced into a 0.2-L kneader, and were mixed uniformly. Then, 28 g of diethylene glycol was gradually injected therein, the content was kneaded and maintained in a dough form, and pulverization was carried out for 5 hours at 5 degrees C. in an argon gas atmosphere. Subsequently, the content was placed in 1 L of a 0.1 mol/L aqueous solution of acetic acid, and the mixture was uniformly dispersed with a homogenizer. The dispersion was then filtered and washed with water, and the resulting wet cake was dried under reduced pressure at 40 degrees C., to obtain 11.8 g of the quinolinone derivative having an average particle diameter of 85 nm.

Comparative Example 6

Pulverization of the quinolinone derivative [7-(3,5-dimethoxy-4-hydroxycinnamoylamino)-3-octyloxy-4-hydroxy-1-methyl-2(1H)-quinolinone] was performed in the same manner as in Comparative Example 1. The average particle diameter of the resulting quinolinone derivative was 620 nm.

Comparative Example 7

Fine pulverization of the quinolinone derivative [7-(3,5-dimethoxy-4-hydroxycinnamoylamino)-3-octyloxy-4-hydroxy-1-methyl-2(1H)-quinolinone] was carried out according to the method described in the Patent Document 8. 1 g of the quinolinone derivative having an average particle diameter of 1,280 nm, and 9 g of D-mannitol were introduced into a vibrating sample mill (TI-100, manufactured by Heiko Seisakusho, Ltd.; 100-mL alumina vessel, milling rod; a cylindrical type with diameter 35 mm×49 mm made of alumina), and were mixed uniformly. Milling was performed for 60 minutes. Subsequently, the content was placed in 100 mL of a 0.1 mol/L aqueous solution of acetic acid containing 9 g of dissolved sodium chloride, and the mixture was uniformly dispersed with a homogenizer. The dispersion was then filtered and washed with water, and the resulting wet cake was dried under reduced pressure at 40 degrees C., to obtain 0.8 g of the quinolinone derivative having an average particle diameter of 128 nm. Additionally, D-mannitol is a sugar alcohol described in the method described in the Patent Document 8, such that D-mannitol can finely pulverize a poorly soluble compound most satisfactorily.

Example 9

10.0 g of miconazole (melting point: 84 to 87 degrees C.) having an average particle diameter of 10,900 nm, and 100.0 g of pulverized sodium chloride (average particle diameter 5 μm) were introduced into a 0.2-L kneader, and were mixed uniformly. Then, 21.0 g of glycerin was gradually injected therein, the content was kneaded and maintained in a dough form, and pulverization was carried out for 18 hours at 20 degrees C. Subsequently, the content was rapidly cooled with liquid nitrogen and was placed in 1 L of distilled water cooled to 5 degrees C., and the mixture was uniformly dispersed with an ultrasonic apparatus (UT-105, manufactured by Sharp Manufacturing System Corporation). The dispersion was then filtered and washed using distilled water at 5 degrees C., and the resulting wet cake was redispersed by an ultrasonic apparatus, and then freeze-dried, to obtain 6.7 g of miconazole having an average particle diameter of 295 nm.

Comparative Example 8

Pulverization of miconazole was performed in the same manner as in Comparative Example 1. The average particle diameter of the resulting miconazole was 651 nm.

Example 10

6.8 g of ketoprofen (melting point: 94 to 97 degrees C.) having an average particle diameter of 3,010 nm, and 105.6 g of pulverized sodium chloride (average particle diameter 5 μm) were introduced into a 0.2-L kneader, and were mixed uniformly. Then, 25.3 g of glycerin was gradually injected therein, the content was kneaded and maintained in a dough form, and pulverization was carried out for 18 hours at 20 degrees C. Subsequently, the content was rapidly cooled with liquid nitrogen and was placed in 1 L of distilled water that had been cooled to 5 degrees C., and the mixture was uniformly dispersed with an ultrasonic apparatus (UT-105, manufactured by Sharp Manufacturing System Corporation). The dispersion was then filtered and washed using distilled water at 5 degrees C., and the resulting wet cake was redispersed by an ultrasonic apparatus, and then freeze-dried, to obtain 4.8 g of ketoprofen having an average particle diameter of 285 nm.

Comparative Example 9

Pulverization of ketoprofen was performed in the same manner as in Comparative Example 1. The average particle diameter of the resulting ketoprofen was 1,136 nm.

Example 11

8.86 g of fluticasone propionate (melting point: about 273 degrees C. (decomposed)) having an average particle diameter of 7,850 nm, and 141.6 g of pulverized sodium chloride (average particle diameter 5 μm) were introduced into a 0.2-L kneader, and were mixed uniformly. Then, 28.7 g of glycerin was gradually injected therein, the content was kneaded and maintained in a dough form, and pulverization was carried out for 12 hours at 10 degrees C. Subsequently, the content was placed in 1000 mL of a 0.1 mol/L aqueous solution of acetic acid, and the mixture was uniformly dispersed with a homogenizer. The dispersion was then filtered and washed with water, and the resulting wet cake was dried under reduced pressure at 20 degrees C., to obtain 8.0 g of fluticasone propionate having an average particle diameter of 185 nm.

Comparative Example 10

Pulverization of fluticasone propionate was performed in the same manner as in Comparative Example 1. The average particle diameter of the resulting fluticasone propionate was 438 nm.

Example 12

8 g of pranlukast hydrate (melting point: about 231 to 235 degrees C. (decomposed)) having an average particle diameter of 1,088 nm, and 155 g of pulverized sodium chloride (average particle diameter 5 μm) were introduced and were mixed uniformly. Then, 39.5 g of glycerin was gradually injected therein, the content was kneaded and maintained in a dough form, and pulverization was carried out for 8 hours at 20 degrees C. Subsequently, the content was placed in 1000 mL of distilled water, and the mixture was uniformly dispersed using an ultrasonic apparatus (UT-105, manufactured by Sharp Manufacturing System Corporation). The dispersion was then filtered and washed with water, and the resulting wet cake was dried under reduced pressure at 20 degrees C., to obtain 7.1 g of pranlukast hydrate having an average particle diameter of 78 nm.

Comparative Example 11

Pulverization of pranlukast hydrate was performed in the same manner as in Comparative Example 1. The average particle diameter of the resulting pranlukast hydrate was 577 nm.

Example 13

8 g of dexamethasone (melting point: about 245 degrees C. (decomposed)) having an average particle diameter of 1,249 nm, and 128 g of pulverized sodium chloride (average particle diameter 5 μm) were introduced and were mixed uniformly. Then, 31.2 g of glycerin was gradually injected therein, the content was kneaded and maintained in a dough form, and pulverization was carried out for 8 hours at 20 degrees C. Subsequently, the content was placed in 1000 mL of a 0.1 mol/L aqueous solution of acetic acid, and the mixture was uniformly dispersed using an ultrasonic apparatus (UT-105, manufactured by Sharp Manufacturing System Corporation). The dispersion was then filtered and washed with water, and the resulting wet cake was dried under reduced pressure at 20 degrees C., to obtain 6.5 g of dexamethasone having an average particle diameter of 168 nm.

Comparative Example 12

Pulverization of dexamethasone was performed in the same manner as in Comparative Example 1. The average particle diameter of the resulting dexamethasone was 727 nm.

Example 14

8 g of zafirlukast (melting point: about 200 degrees C. (decomposed)) having an average particle diameter of 5,347 nm, and 128 g of pulverized sodium chloride (average particle diameter 5 μm) were introduced and were mixed uniformly. Then, 40 g of glycerin was gradually injected therein, the content was kneaded and maintained in a dough form, and pulverization was carried out for 8 hours at 20 degrees C. Subsequently, the content was placed in 1000 mL of a 0.1 mol/L aqueous solution of acetic acid, and the mixture was uniformly dispersed using an ultrasonic apparatus (UT-105, manufactured by Sharp Manufacturing System Corporation). The dispersion was then filtered and washed with water, and the resulting wet cake was dried under reduced pressure at 20 degrees C., to obtain 7.2 g of zafirlukast having an average particle diameter of 149 nm.

Comparative Example 13

Pulverization of zafirlukast was performed in the same manner as in Comparative Example 1. The average particle diameter of the resulting zafirlukast was 558 nm.

As it is obvious when Examples 1 to 14 and Comparative Examples 1 to 13 are compared, it is clear that finely pulverized organic compound particles having a markedly small average particle diameter than that obtained by a conventional method, may be obtained by the method for producing finely pulverized organic compound particles of the present invention.

2. Trituration Using Hoover Muller

Example 15

0.1 g of ketoprofen (melting point: 94 to 97 degrees C.) having an average particle diameter of 3,010 nm, and 1.6 g of pulverized sodium chloride (average particle diameter 5 μm) were introduced into a water-cooling type Hoover muller, and were mixed uniformly. Then, 0.45 g of glycerin was slowly added dropwise, the content was kneaded and maintained in a dough form, and pulverization was carried out by kneading 100 cycles at 20 degrees C. Subsequently, the content was rapidly cooled with liquid nitrogen and placed in distilled water that had been cooled to 5 degrees C., and the mixture was uniformly dispersed with an ultrasonic apparatus (TU-105, manufactured by Sharp Manufacturing System Corporation). The dispersion was then filtered and washed with water (distilled water at 5 degrees C.), and the resulting wet cake was redispersed by the ultrasonic apparatus and then freeze-dried, to obtain 0.07 g of ketoprofen having an average particle diameter of 289 nm.

Example 16

0.1 g of pranlukast hydrate (melting point: about 231 to 235 degrees C. (decomposed)) having an average particle diameter of 1,088 nm, and 1.6 g of pulverized sodium chloride (average particle diameter 5 μm) were introduced into a water-cooling type Hoover muller, and were mixed uniformly. Then, 0.55 g of glycerin was slowly added dropwise, the content was kneaded and maintained in a dough form, and pulverization was carried out by kneading 100 cycles at 20 degrees C. Subsequently, the content was placed in 50 mL of distilled water, and was uniformly dispersed with an ultrasonic apparatus (TU-105, manufactured by Sharp Manufacturing System Corporation). The dispersion was then filtered and washed with water, and the resulting wet cake was dried under reduced pressure at 20 degrees C., to obtain 0.07 g of pranlukast hydrate having an average particle diameter of 73 nm.

As it is obvious when Example 10 is compared with Example 15, and Example 12 is compared with Example 15, it was clear that there was almost no difference in the average particle diameter obtained by a water-cooling type Hoover muller and a kneader as the trituration apparatus. Therefore, it was shown that according to the method of the present invention, even when different types of apparatuses for forming fine particles are used, fine pulverization of organic compounds for medical use can be carried out.

3. Influence of Viscosity of Polyol and Addition of Viscosity Modifier on Pulverization Efficiency The following experiment was carried out to investigate the influence exerted by the viscosity of the polyol or the viscosity modifier during the fine pulverization process of organic compounds for medical use.

Example 17

0.1 g of fluticasone propionate (melting point: about 273 degrees C. (decomposed)) having an average particle diameter of 7,850 nm, and 1.6 g of pulverized sodium chloride (average diameter 2 μm) were introduced into a water-cooling type Hoover muller, and were mixed uniformly. Then, 0.62 g of glycerin (viscosity: 20 degrees C., 1,500 mPa·s) was slowly added dropwise, the content was kneaded and maintained in a dough form, and pulverization was carried out by kneading 100 cycles at 20 degrees C. Subsequently, the content was placed in 50 mL of a 0.1 mol/L aqueous solution of acetic acid, and was uniformly dispersed with an ultrasonic apparatus (TU-105, manufactured by Sharp Manufacturing System Corporation). The dispersion was then filtered and washed with water, and the resulting wet cake was dried under reduced pressure at 20 degrees C., to obtain 0.075 g of fluticasone propionate having an average particle diameter of 114 nm.

Example 18

0.1 g of fluticasone propionate (melting point: about 273 degrees C. (decomposed)) having an average particle diameter of 7,850 nm, and 1.6 g of pulverized sodium chloride (average diameter 2 μm) were introduced into a water-cooling type Hoover muller, and were mixed uniformly. Then, 0.62 g of glycerin (viscosity: 10 degrees C., 4,300 mPa·s) was slowly added dropwise, the content was kneaded and maintained in a dough form, and pulverization was carried out by kneading 100 cycles at 10 degrees C. Subsequently, the content was placed in 50 mL of a 0.1 mol/L aqueous solution of acetic acid, and was uniformly dispersed with an ultrasonic apparatus (TU-105, manufactured by Sharp Manufacturing System Corporation). The dispersion was then filtered and washed with water, and the resulting wet cake was dried under reduced pressure at 20 degrees C., to obtain 0.077 g of fluticasone propionate having an average particle diameter of 108 nm.

Example 19

0.1 g of fluticasone propionate (melting point: about 273 degrees C. (decomposed)) having an average particle diameter of 7,850 nm, and 1.6 g of pulverized sodium chloride (average diameter 2 μm) were introduced into a water-cooling type Hoover muller, and were mixed uniformly. Then, 0.48 g of a viscous liquid of glycerin containing 30% by weight of citric acid (viscosity: 20 degrees C., 13,000 mPa·s) was slowly added dropwise, the content was kneaded and maintained in a dough form, and pulverization was carried out by kneading 100 cycles at 20 degrees C. Subsequently, the content was placed in 50 mL of a 0.1 mol/L aqueous solution of acetic acid, and was uniformly dispersed with an ultrasonic apparatus (TU-105, manufactured by Sharp Manufacturing System Corporation). The dispersion was then filtered and washed with water, and the resulting wet cake was dried under reduced pressure at 20 degrees C., to obtain 0.076 g of fluticasone propionate having an average particle diameter of 103 nm.

Example 20

0.1 g of fluticasone propionate (melting point: about 273 degrees C. (decomposed)) having an average particle diameter of 7,850 nm, and 1.6 g of pulverized sodium chloride (average diameter 2 μm) were introduced into a water-cooling type Hoover muller, and were mixed uniformly. Then, 0.40 g of a viscous liquid of glycerin containing 30% by weight of citric acid (viscosity: 10 degrees C., 30,000 mPa·s) was slowly added dropwise, the content was kneaded and maintained in a dough form, and pulverization was carried out by kneading 100 cycles at 10 degrees C. Subsequently, the content was placed in 50 mL of a 0.1 mol/L aqueous solution of acetic acid, and was uniformly dispersed with an ultrasonic apparatus (TU-105, manufactured by Sharp Manufacturing System Corporation). The dispersion was then filtered and washed with water, and the resulting wet cake was dried under reduced pressure at 20 degrees C., to obtain 0.075 g of fluticasone propionate having an average particle diameter of 94 nm.

Example 21

0.1 g of fluticasone propionate (melting point: about 273 degrees C. (decomposed) ) having an average particle diameter of 7,850 nm, and 1.6 g of pulverized sodium chloride (average diameter 2 μm) were introduced into a water-cooling type Hoover muller, and were mixed uniformly. Then, 0.61 g of a viscous liquid of glycerin containing 50% by weight of citric acid (viscosity: 20 degrees C., 70,000 mPa·s) was slowly added dropwise, the content was kneaded and maintained in a dough form, and pulverization was carried out by kneading 100 cycles at 20 degrees C. Subsequently, the content was placed in 50 mL of a 0.1 mol/L aqueous solution of acetic acid, and was uniformly dispersed with an ultrasonic apparatus (TU-105, manufactured by Sharp Manufacturing System Corporation). The dispersion was then filtered and washed with water, and the resulting wet cake was dried under reduced pressure at 20 degrees C., to obtain 0.078 g of fluticasone propionate having an average particle diameter of 92 nm.

Example 22

0.1 g of fluticasone propionate (melting point: about 273 degrees C. (decomposed)) having an average particle diameter of 7,850 nm, and 1.6 g of pulverized sodium chloride (average diameter 2 μm) were introduced into a water-cooling type Hoover muller, and were mixed uniformly. Then, 0.61 g of a viscous liquid of glycerin containing 50% by weight of citric acid (viscosity: 10 degrees C., 180,000 mPa·s) was slowly added dropwise, the content was kneaded and maintained in a dough form, and pulverization was carried out by kneading 100 cycles at 10 degrees C. Subsequently, the content was placed in 50 mL of a 0.1 mol/L aqueous solution of acetic acid, and was uniformly dispersed with an ultrasonic apparatus (TU-105, manufactured by Sharp Manufacturing System Corporation). The dispersion was then filtered and washed with water, and the resulting wet cake was dried under reduced pressure at 20 degrees C., to obtain 0.072 g of fluticasone propionate having an average particle diameter of 70 nm.

Example 23

0.1 g of fluticasone propionate (melting point: about 273 degrees C. (decomposed)) having an average particle diameter of 7,850 nm, and 1.6 g of pulverized sodium chloride (average diameter 5 μm) were introduced into a water-cooling type Hoover muller, and were mixed uniformly. Then, 0.38 g of a viscous liquid of polyethylene glycol 400 containing 33% by weight of citric acid (viscosity: 20 degrees C., 15,000 mPa·s) was slowly added dropwise, the content was kneaded and maintained in a dough form, and pulverization was carried out by kneading 100 cycles at 20 degrees C. Subsequently, the content was placed in 50 mL of a 0.1 mol/L aqueous solution of acetic acid, and was uniformly dispersed with an ultrasonic apparatus (TU-105, manufactured by Sharp Manufacturing System Corporation). The dispersion was then filtered and washed with water, and the resulting wet cake was dried under reduced pressure at 20 degrees C., to obtain 0.072 g of fluticasone propionate having an average particle diameter of 109 nm.

From the results of Examples 17 to 23, it is clear that when the viscosity of the polyol is increased by controlling the temperature and adding a viscosity modifier, the obtainable average particle diameter is decreased.

4. Pulverization Using Organic Compounds Having Low Melting Point

In order to confirm that the method of the present invention is adequate for compounds having high melting point, formation of fine particles according to the method of the present invention was carried out using ibuprofen, which has a melting point of 75 to 77 degrees C.

Comparative Example 14

7.7 g of ibuprofen (melting point: 75 to 77 degrees C.) having an average particle diameter of 18,050 nm, and 143 g of pulverized sodium chloride were introduced into a 0.2-L kneader, and were mixed uniformly. Then, 30 g of glycerin was gradually injected therein, the content was kneaded and maintained in a dough form, and pulverization was carried out for 8 hours at −10 degrees C. Subsequently, the content was placed in 500 mL of a 0.1 mol/L aqueous solution of acetic acid, and the mixture was uniformly dispersed with a homogenizer. The dispersion was then filtered and washed with water, and the resulting wet cake was dried under reduced pressure at 40 degrees C., to obtain 6.3 g of the ibuprofen having an average particle diameter of 1,900 nm.

When Examples 1 to 14 and Comparative Example 14 are compared, it is clear that the production method of the present invention can obtain finely pulverized organic compound particles having a smaller average particle diameter, in the case of forming finely particles of an organic compound having a melting point of 80 degrees or more.

5. Pulverization Effect of When Other Polyols are Used as Liquid Pulverization Aid In order to confirm whether polyols other than glycerin can also be used as the pulverization aid that is used for the method of the present invention, a fine pulverization test using various polyols was performed.

Example 24

Finely pulverized organic compound particles of cortisone acetate were obtained, all in the same manner as in Example 3, except that the polyols described in Table 1 were used.

TABLE 1

| Polyol | Ave. Diameter before pulverization (nm) | Ave. Diameter after pulverization (nm) |
|---|---|---|
| Diethylene glycol | 1,060 | 480 |
| Polyethylene glycol | 1,060 | 590 |
| Propylene glycol | 1,060 | 450 |
| Glycerin | 1,060 | 260 |

The obtained average particle diameters of cortisone acetate are presented in Table 1. From these results, it is clear that even if any polyol among glycerin, propylene glycol, polyethylene glycol and diethylene glycol is used, finely pulverized organic compound particles having a sufficient and satisfactory average particle diameter may be obtained. In addition, it is also clear that glycerin is suitable as the polyol used in the fine pulverization of cortisone acetate.

6. Pulverization Effect of the Case Where D-Mannitol is Used as Solid Pulverization Aid Nifedipine was pulverized using D-mannitol as a physiologically acceptable substance other than a salt, as the solid pulverization aid.

Comparative Example 15

Pulverization of nifedipine was carried out, all in the same manner as in Example 2, except that D-mannitol was used instead of sodium chloride. The obtained average particle diameter of nifedipine was 890 nm.

As it is obvious when the results of Example 2, Comparative Example 2 and Comparative Example 12 are compared, when D-mannitol was used, only average particle diameters that were comparable to the average particle diameters obtained by the conventional jet mill pulverization method could be obtained. Therefore, it is clear that the method of using a salt as the pulverization aid is a method resulting in excellent fine pulverization.

7. Measurement of Crystallinity of Finely Pulverized Organic Compounds

Test Example 1

Each crystallinity of the quinolinone derivative before being finely pulverized, the quinolinone derivative obtained in Example 8 and the quinolinone derivative obtained in Comparative Example 8, was examined using an X-ray diffraction measurement apparatus (D8 Discover, manufactured by Bruker AXS, Inc.

Figure 1B:
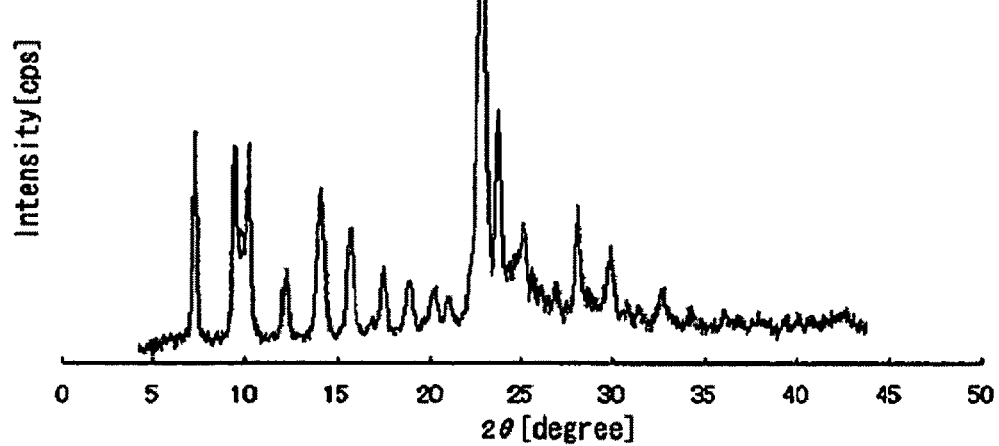
FIG. 1B is a diagram showing the results of X-ray diffraction obtained in Test Example 1, with the vertical axis representing the intensity, and the horizontal axis representing the diffraction angle.
Figure 1C:
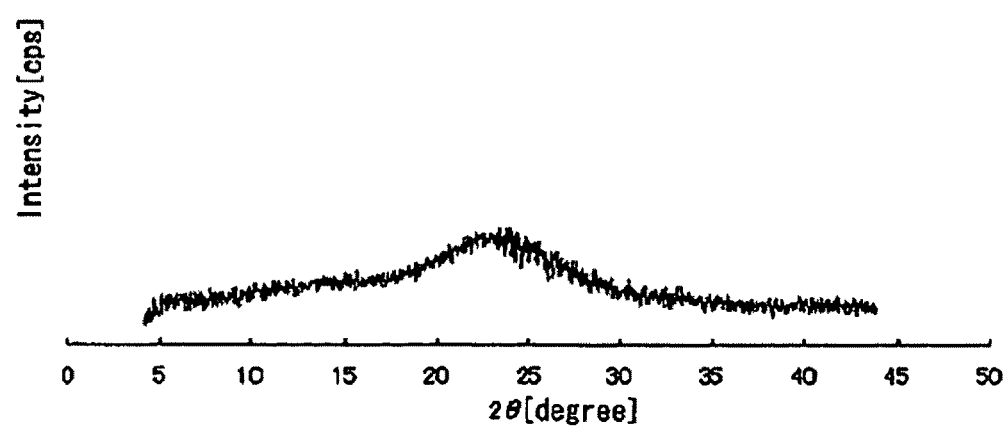
FIG. 1C is a diagram showing the results of X-ray diffraction obtained in Test Example 1, with the vertical axis representing the intensity, and the horizontal axis representing the diffraction angle.

FIG. 1 is a diagram showing the obtained X-ray diffraction results, with the vertical axis representing the intensity, and the horizontal axis representing the diffraction angle. FIG. 1A shows the results for the quinolinone derivative before being finely pulverized; FIG. 1B shows the results for the quinolinone derivative obtained in Example 8; and FIG. 1C shows the results for the quinolinone derivative obtained in Comparative Example 8. The quinolinone derivative obtained in Example 8 produced almost the same results as those produced by the quinolinone derivative before being finely pulverized, and it is obvious that the derivatives have crystalline structures. On the other hand, the quinolinone derivative obtained in Comparative Example 8 had almost no peak detected, and was confirmed to be amorphous. That is, it is clear that unlike the conventional methods, very useful finely pulverized organic compound particles which have the crystal structure well maintained and also have high chemical stability, can be produced by the method for producing finely pulverized organic compound particles of the present invention.

8. Production of Porous Fine Particles

Example 25

To 10 g of a wet cake of the quinolinone derivative (solids ratio is 30%) obtained in the same manner as in Example 8, 0.36 g of L-isoleucine and 8.4 mL of purified water were added, and the mixture was made uniform using an ultrasonic apparatus (UT-105, manufactured by Sharp Manufacturing System Corporation), to obtain 18.76 g of a suspension. 3 g of the obtained suspension was sprayed into 500 mL of liquid nitrogen contained in a 2-L stainless steel vessel, using a two-fluid nozzle spray (standard nozzle for Pulvis Mini Spray type GA-31, manufactured by Yamato Scientific Co., Ltd.), and thus, frozen particles were obtained. The obtained frozen particles were freeze-dried, and 0.35 g of a powder of the quinolinone derivative was obtained. Photographs of the obtained powder were taken using an electron microscope (Type VE-7800, manufactured by Keyence Corp.).

Figure 2:
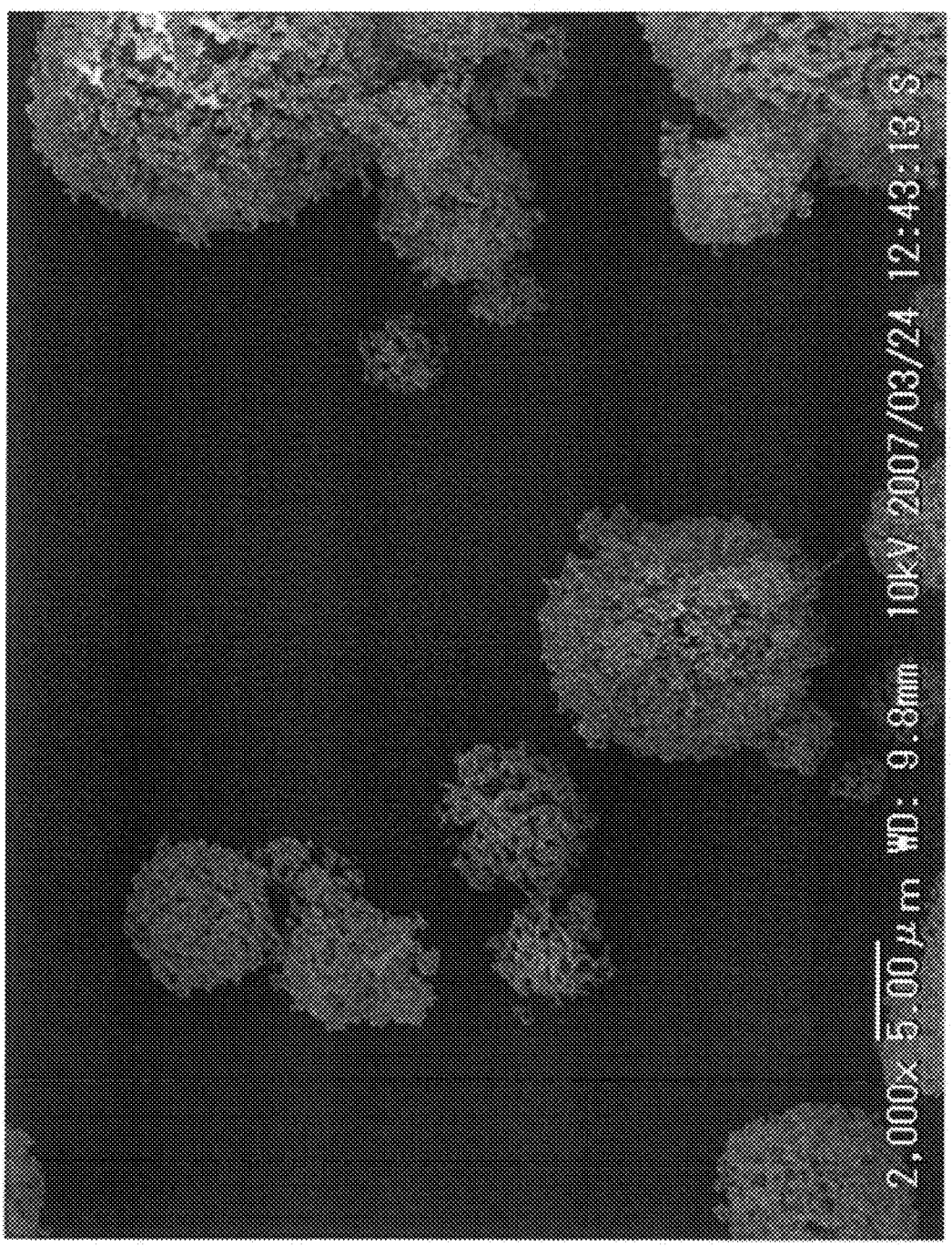
FIG. 2 is an electron microscopic photograph of the quinolinone derivative powder obtained in Example 10.

FIG. 2 is an electron microscopic photograph of the obtained powder. It is clear from FIG. 2 that the powder consists of assemblages of porous spherical fine particles having a particle diameter of about 1 to 20 μm. That is, it is conceived that the finely pulverized organic compound particles obtained by the method for producing finely pulverized organic compound particles of the present invention have good fluidity and satisfactory redispersibility in water, and therefore, the particles exhibit excellent characteristics as an inhalant, an injectable preparation and an oral preparation.

Example 26

1.6 g of the powder of the quinolinone derivative obtained by Example 8, and 0.1 g of carmellose sodium were added to 10.8 mL of purified water, and the mixture was made uniform using an ultrasonic apparatus (UT-105, manufactured by Sharp Manufacturing System Corporation), to obtain 12.5 g of a suspension. 3 g of the obtained suspension was sprayed into liquid nitrogen in the same manner as in Example 25, and the obtained frozen particles were freeze-dried. Thus, 0.28 g of a powder of the quinolinone derivative was obtained.

Figure 3:
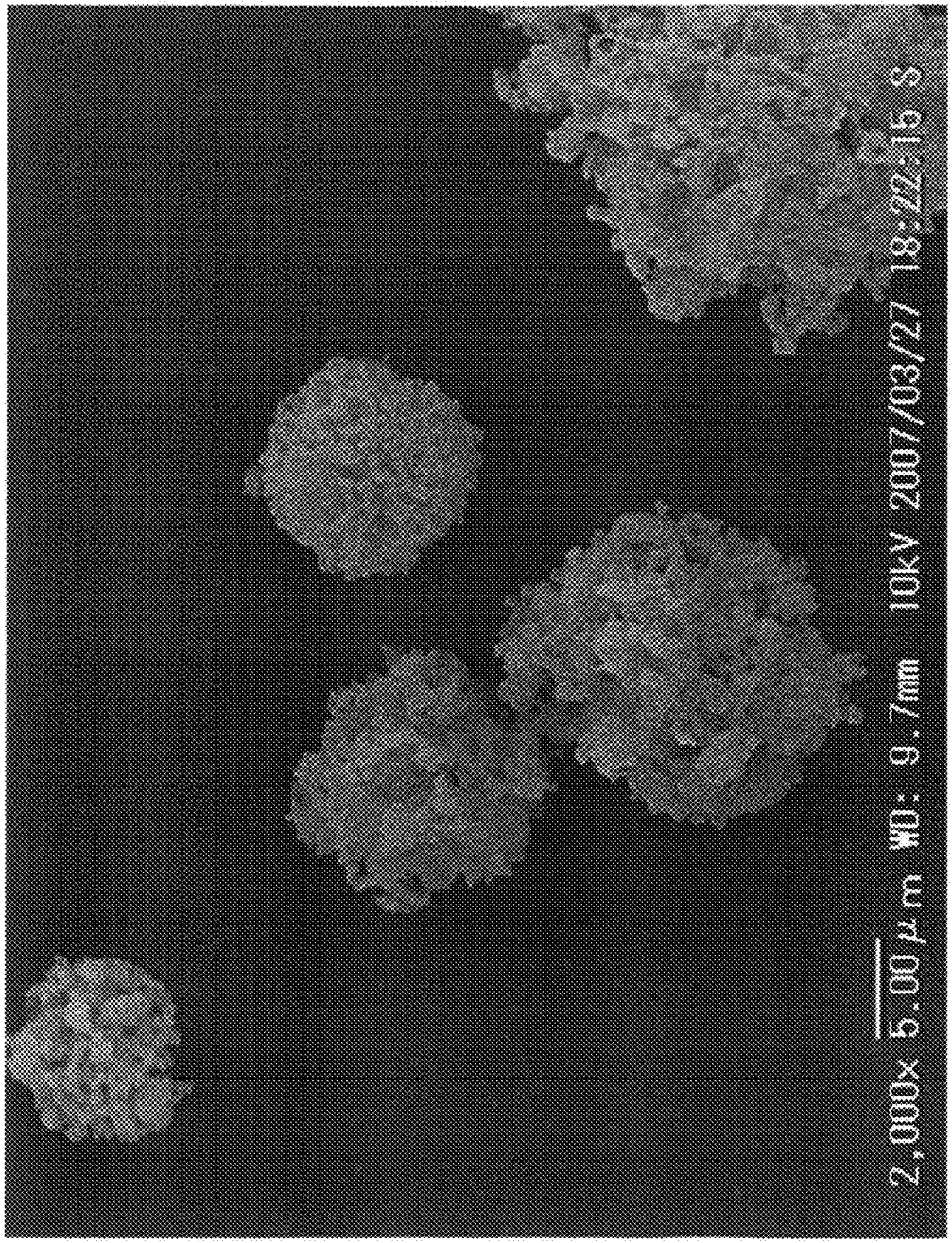
FIG. 3 is an electron microscopic photograph of the quinolinone derivative powder obtained in Example 11.

FIG. 3 is an electron microscopic photograph of the obtained powder. It is clear from FIG. 3 that the powder consists of assemblages of porous spherical fine particles having a particle diameter of about 1 to 20 μm. That is, it is conceived that the finely pulverized organic compound particles obtained by the method for producing finely pulverized organic compound particles of the present invention have good fluidity and satisfactory redispersibility in water, and therefore, the particles exhibit excellent characteristics as an inhalant, an injectable preparation and an oral preparation.

Example 27

To 10 g of a wet cake of the quinolinone derivative (solids ratio is 30%) obtained in the same manner as in Example 8, 1.45 g of ethanol and 14.0 mL of purified water were added, and the mixture was made uniform using an ultrasonic apparatus (UT-105, manufactured by Sharp Manufacturing System Corporation), to obtain 25.45 g of a suspension. 3 g of the obtained suspension was sprayed into 500 mL of liquid nitrogen contained in a 2-L stainless steel vessel, using a two-fluid nozzle spray (standard nozzle for Pulvis Mini Spray type GA-31, manufactured by Yamato Scientific Co., Ltd.), and thus, frozen particles were obtained. The obtained frozen particles were freeze-dried, and 0.26 g of a powder of the quinolinone derivative was obtained. Photographs of the obtained powder were taken using an electron microscope (Type VE-7800, manufactured by Keyence Corp.).

Figure 4:
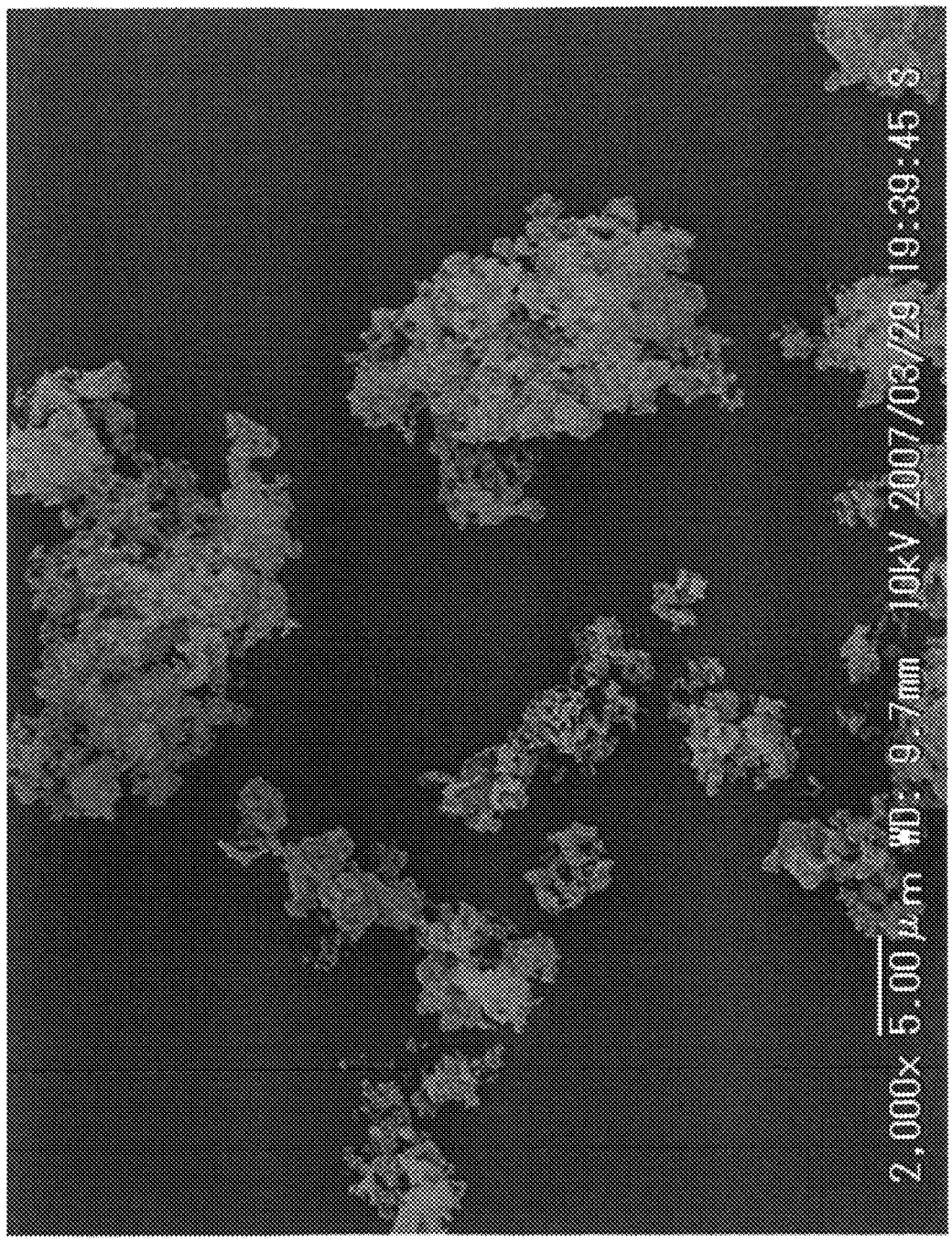
FIG. 4 is an electron microscopic photograph of the quinolinone derivative powder obtained in Example 12.

FIG. 4 is an electron microscopic photograph of the obtained powder. It is clear from FIG. 4 that the powder consists of assemblages of porous irregular-shaped fine particles having a particle diameter of about 1 to 20 μm. That is, it is conceived that the finely pulverized organic compound particles obtained by the method for producing finely pulverized organic compound particles of the present invention exhibit excellent characteristics as an inhalant.

Example 28

3 g of the suspension of the quinolinone derivative obtained in the same manner as in Example 26 was freeze-dried, and 0.38 g of a powder of the quinolinone derivative was obtained.

It is conceived that the obtained powder exhibits excellent characteristics as an inhalant, an injectable preparation and an oral preparation.

Example 29

To 10 g of a wet cake of nifedipine (solids ratio is 30%) obtained in the same manner as in Example 2, 0.1 g of dioctyl sodium sulfosuccinate, 0.1 g of polyvinyl alcohol, 0.52 g of L-valine and 0.5 mL of purified water were added, and the mixture was made uniform using an ultrasonic apparatus (UT-105, manufactured by Sharp Manufacturing System Corporation), to obtain 11.22 g of a suspension. 3 g of the obtained suspension was sprayed into liquid nitrogen in the same manner as in Example 25, and the obtained frozen particles were freeze-dried. Thus, 0.3 g of a powder of nifedipine was obtained.

Figure 5:
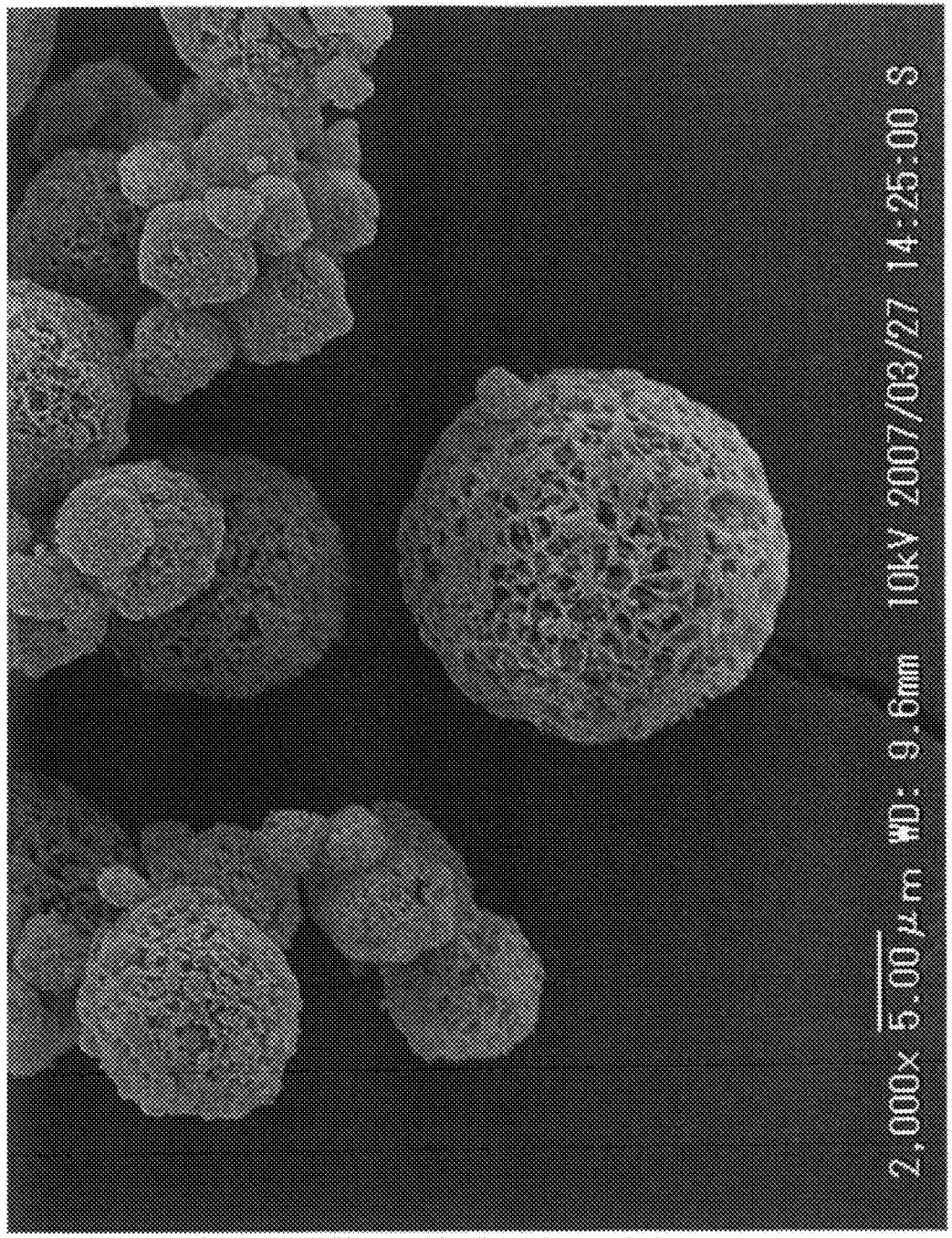
FIG. 5 is an electron microscopic photograph of the nifedipine powder obtained in Example 14.

FIG. 5 is an electron microscopic photograph of the obtained powder. It is clear from FIG. 5 that the powder consists of assemblages of porous spherical fine particles having a particle diameter of about 1 to 20 μm. That is, it is conceived that the finely pulverized organic compound particles obtained by the method for producing finely pulverized organic compound particles of the present invention have good fluidity and satisfactory redispersibility in water, and therefore, the particles exhibit excellent characteristics as an inhalant, an injectable preparation and an oral preparation.

Example 30

To 10 g of a wet cake of nifedipine (solids ratio is 30%) obtained in the same manner as in Example 2, 0.03 g of carmellose sodium, 0.47 g of D-sorbitol, 0.0012 g of Polysorbate 80, and 19 mL of purified water were added, and the mixture was made uniform using an ultrasonic apparatus (UT-105, manufactured by Sharp Manufacturing System Corporation), to obtain 29.50 g of a suspension. It is conceived that the obtained suspension exhibits excellent characteristics as an injectable preparation and an oral preparation.

Example 31

To 10 g of a wet cake of fluticasone propionate (solids ratio is 30%) obtained in the same manner as in Example 11, 1.0 g of ethanol and 39.0 mL of purified water were added, and the mixture was made uniform using an ultrasonic apparatus (UT-105, manufactured by Sharp Manufacturing System Corporation), to obtain 50.0 g of a suspension. 3 g of the obtained suspension was sprayed into 500 mL of liquid nitrogen contained in a 2-L stainless steel vessel, using a two-fluid nozzle spray (standard nozzle for Pulvis MiniSpray type GA-31, manufactured by Yamato Scientific Co., Ltd.), and thus, frozen particles were obtained. The obtained frozen particles were freeze-dried, and 0.13 g of a powder of fluticasone propionate was obtained. Photographs of the obtained powder were taken using an electron microscope (Type VE-7800, manufactured by Keyence Corp.). An electron microscopic photograph of the powder is presented in FIG. 6.

Example 32

10 g of a suspension of fluticasone propionate obtained in the same manner as in Example 31 was dried using a spray drying apparatus (Pulvis Mini Spray GB-21, manufactured by Yamato Scientific Co., Ltd.), to obtain 0.18 g of a powder of fluticasone propionate. Photographs of the obtained powder were taken using an electron microscope (Type VE-7800, manufactured by Keyence Corp.). An electron microscopic photograph of the powder is presented in FIG. 7.

Figure 6:
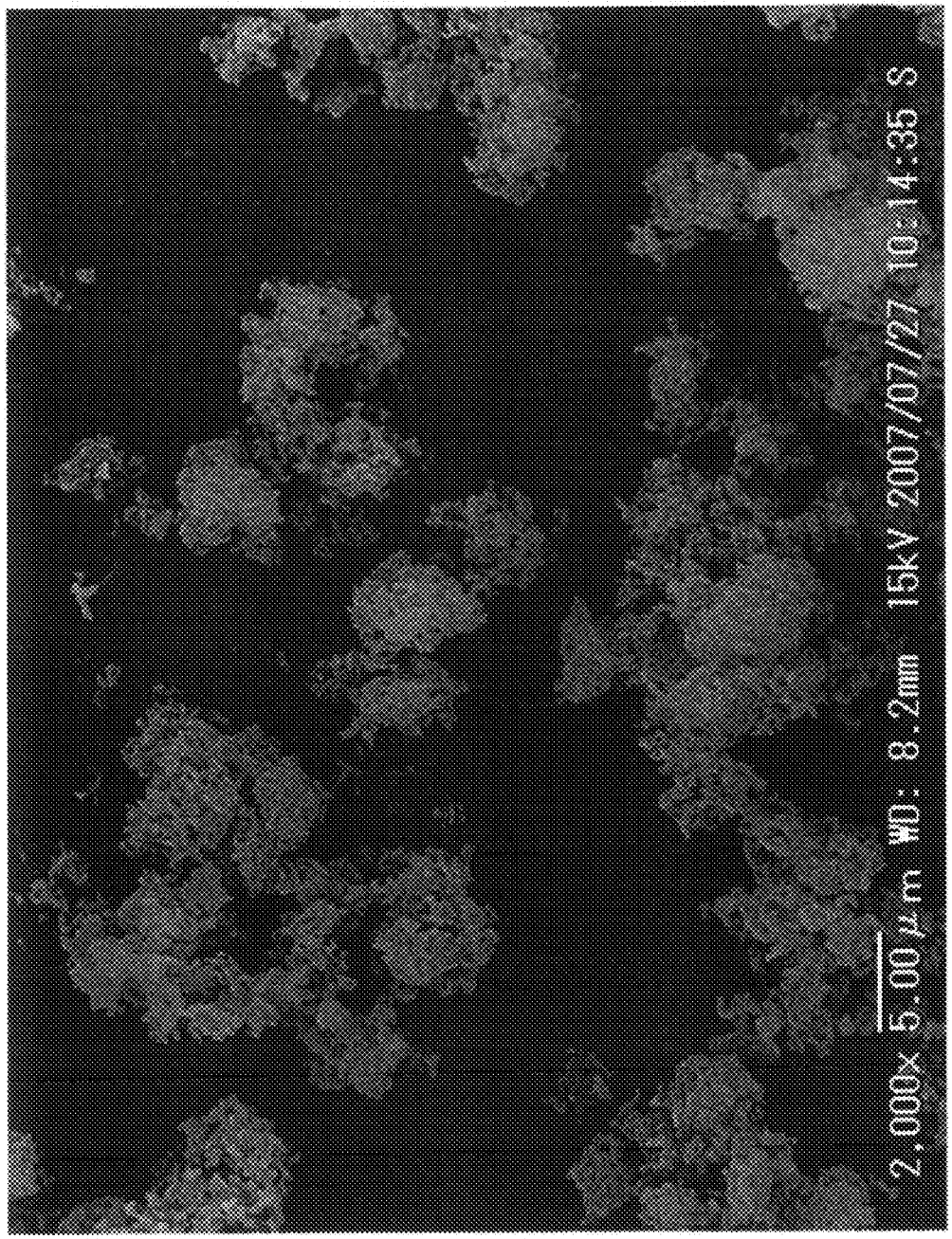
FIG. 6 is an electron microscopic photograph of the fluticasone propionate powder obtained in Example 19.
Figure 7:
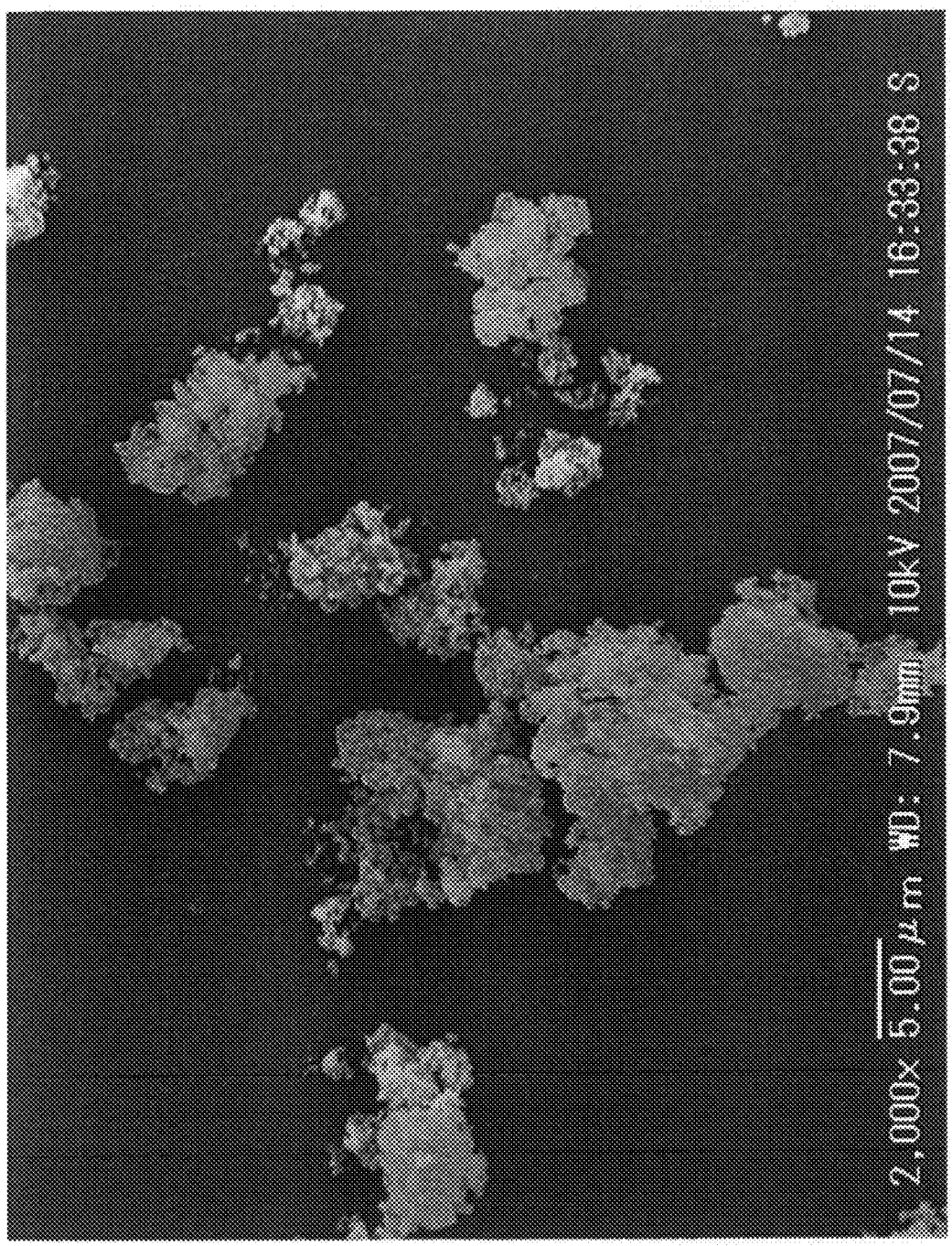
FIG. 7 is an electron microscopic photograph of the fluticasone propionate powder obtained in Example 20.

It is clear from FIGS. 6 and 7 that the powders obtained in Examples 31 and 32 consist of porous irregular-shaped fine particles having a particle diameter of about 1 to 20 μm. That is, it is conceived that the finely pulverized organic compound particles obtained by the method for producing finely pulverized organic compound particles of the present invention exhibit excellent characteristics as an inhalant.

9. Measurement of Particle Size Distribution

Since the stability of the suspension of the finely pulverized organic compound depends not only on the average particle diameter, but also on the particle size distribution, the particle size distributions of the organic compounds obtained by the method of the present invention were measured.

Example 33

To 0.5 g of a wet cake of fluticasone propionate (solids ratio is 30%) obtained in the same manneras in Example 22, 0.024 g of benzalkonium chloride, 0.48 g of polyvinylpyrrolidone, 4.8 g of glycerin, and 4.696 g of purified water were added, and the mixture was made uniform using an ultrasonic apparatus (UT-105, manufactured by Sharp Manufacturing System Corporation). 89.5 g of purified water was further added to obtain 100.0 g of a suspension. The particle size distribution of the obtained suspension was measured using a particle size distribution analyzer (Microtrac UPA, manufactured by Nikkiso Co., Ltd.), and as a result, a particle distribution with an average particle diameter of 164 nm, a median particle diameter 148 nm, and a 90% median diameter of 263 nm, was obtained.

Comparative Example 16

To 0.15 g of fluticasone propionate obtained in the same manner as in Comparative Example 10, 0.024 g of benzalkonium chloride, 0.48 g of polyvinylpyrrolidone, 4.8 g of glycerin, and 4.696 g of purified water were added, and the mixture was made uniform using an ultrasonic apparatus (UT-105, manufactured by Sharp Manufacturing System Corporation). 89.85 g of purified water was further added to obtain 100.0 g of a suspension. The particle size distribution of the obtained suspension was measured using a particle size distribution analyzer (Microtrac MT-3000, manufactured by Nikkiso Co., Ltd.), and as a result, a particle distribution with an average particle diameter of 2822 nm, a median particle diameter 2369 nm, and a 90% median diameter of 4889 nm, was obtained.

Example 34

To 1.67 g of a wet cake of pranlukast hydrate (solids ratio is 30%) obtained in the same manner as in Example 12, 0.1 g of Polysorbate 80, 0.25 g of methylcellulose, and 4.65 g of purified water were added, and the mixture was made uniform using an ultrasonic apparatus (UT-105, manufactured by Sharp Manufacturing System Corporation). 43.33 g of purified water was further added to obtain 50.0 g of a suspension. The particle size distribution of the obtained suspension was measured using a particle size distribution analyzer (Microtrac UPA, manufactured by Nikkiso Co., Ltd.), and as a result, a particle distribution with an average particle diameter of 197 nm, a median particle diameter 193 nm, and a 90% median diameter of 245 nm, was obtained.

Comparative Example 17

To 0.5 g of pranlukast hydrate obtained in the same manner as in Comparative Example 11, 0.1 g of Polysorbate 80, 0.25 g of methylcellulose, and 4.65 g of purified water were added, and the mixture was made uniform using an ultrasonic apparatus (UT-105, manufactured by Sharp Manufacturing System Corporation). 44.5 g of purified water was further added to obtain 50.0 g of a suspension. The particle size distribution of the obtained suspension was measured using a particle size distribution analyzer (Microtrac MT-3000, manufactured by Nikkiso Co., Ltd.), and as a result, a particle distribution with an average particle diameter of 2188 nm, a median particle diameter 1778 nm, and a 90% median diameter of 3644 nm, was obtained.

Example 35

To 0.75 g of a wet cake of dexamethasone (solids ratio is 20%) obtained in the same manner as in Example 13, 0.2 g of Polysorbate 80, 0.2 g of methylcellulose, and 9.6 g of purified water were added, and the mixture was made uniform using an ultrasonic apparatus (UT-105, manufactured by Sharp Manufacturing System Corporation). 89.25 g of purified water was further added to obtain 100.0 g of a suspension. The particle size distribution of the obtained suspension was measured using a particle size distribution analyzer (Delsa Nano, manufactured by Beckman Coulter, Inc.), and as a result, a particle distribution with an average particle diameter of 289 nm, a median particle diameter 276 nm, and a 90% median diameter of 407 nm, was obtained.

Comparative Example 18

To 0.15 g of dexamethasone obtained in the same manner as in Comparative Example 12, 0.2 g of Polysorbate 80, 0.2 g of methylcellulose, and 9.6 g of purified water were added, and the mixture was made uniform using an ultrasonic apparatus (UT-105, manufactured by Sharp Manufacturing System Corporation). 89.85 g of purified water was further added to obtain 100.0 g of a suspension. The particle size distribution of the obtained suspension was measured using a particle size distribution analyzer (Delsa Nano, manufactured by Beckman Coulter, Inc.), and as a result, a particle distribution with an average particle diameter of 2527 nm, a median particle diameter 1223 nm, and a 90% median diameter of 6481 nm, was obtained.

Example 36

To 0.5 g of a wet cake of indomethacin (solids ratio is 20%) obtained in the same manner as in Example 1, 0.1 g of Polysorbate 80, 0.1 g of methylcellulose, and 4.8 g of purified water were added, and the mixture was made uniform using an ultrasonic apparatus (UT-105, manufactured by Sharp Manufacturing System Corporation). 44.5 g of purified water was further added to obtain 50.0 g of a suspension. The particle size distribution of the obtained suspension was measured using a particle size distribution analyzer (Microtrac UPA, manufactured by Nikkiso Co., Ltd.), and as a result, a particle distribution with an average particle diameter of 332 nm, a median particle diameter 285 nm, and a 90% median diameter of 396 nm, was obtained.

Comparative Example 19

To 0.1 g of indomethacin obtained in the same manner as in Comparative Example 1, 0.1 g of Polysorbate 80, 0.1 g of methylcellulose, and 4.8 g of purified water were added, and the mixture was made uniform using an ultrasonic apparatus (UT-105, manufactured by Sharp Manufacturing System Corporation). 44.9 g of purified water was further added to obtain 50.0 g of a suspension. The particle size distribution of the obtained suspension was measured using a particle size distribution analyzer (Microtrac MT-3000, manufactured by Nikkiso Co., Ltd.), and as a result, a particle distribution with an average particle diameter of 2,900 nm, a median particle diameter 1,767 nm, and a 90% median diameter of 4,171 nm, was obtained.

10. Test on Stability of Suspension

A stability test was performed for the fine particles that had been subjected to the measurement of particle size distribution, in order to confirm that the fine particles were stable in a suspension. Furthermore, as an evaluation for the use as an injectable preparation or an eye drop, the permeability through a 0.45-μm membrane filter and a 0.2-μm membrane filter was measured.

Example 37

(Suspension Stability Evaluation Test)

50 mL each of the suspensions produced in Examples 33 to 36 and Comparative Examples 16 to 19 was filled in a 50-mL glass vial, and the vials were left to stand under the storage conditions of 20 degrees C. and 40 degrees C. After one month, the suspension stability was evaluated based on the following four grades. The evaluation results are presented in Table 2.

double circular mark: There is no precipitate, and a uniform dispersed state is maintained.

single circular mark: A very small amount of precipitate is recognized, but the suspension reverts to a uniform suspension with one to three inversions.

triangular mark: A precipitate is recognized, and the suspension does not revert to a uniform suspension with one to three inversions.

cross mark: Solid-liquid separation causes the supernatant to be transparent, and the suspension does not revert to a uniform suspension with one to three inversions.

(Filter Permeability Test)

2.5 mL each of the suspensions produced in Examples 33 to 36 and Comparative Examples 16 to 19 was passed through a 0.45-μm membrane filter (mixed cellulose ester) and a 0.2-μm membrane filter (mixed cellulose ester), and the active ingredient was measured. The value was compared with the active ingredient concentration obtained before the pass-through, and thereby the permeability (%) was calculated.

TABLE 2

| Test No. | Suspension stability After 1 month | | Permeability by membrane filter (%) | |
|---|---|---|---|---|
| | 40 degrees C. | 20 degrees C. | 0.45 μm | 0.2 μm |
| Example 33 | ○ | ⊙ | 100 | 93.6 |
| Example 34 | ○ | ○ | 100 | 92.2 |
| Example 35 | ○ | ○ | 100 | 81.7 |
| Example 36 | ○ | ○ | 92.4 | 80.1 |
| Comparative example 16 | X | X | 1.4 | 0.5 |
| Comparative example 17 | X | Δ | 0.9 | 0.8 |
| Comparative example 18 | X | X | 7.8 | 4.2 |
| Comparative example 19 | X | X | 2.5 | 1.3 |

The results are presented in Table 2. It is clear that when the fine particles obtained by the pulverization method of the present invention are used as a suspension preparation, the precipitation of active ingredient is markedly suppressed, and the suspension stability is enhanced, as compared to the powder fine particles prepared by conventional methods. It is also clear that since the fine particles can be subjected to filter sterilization for eye drops and injectable preparations because of the high filter permeability of the particles, efficient production and formulation of preparations that are capable of withstanding practical use, can be made possible.

11. Inhalation Property Evaluation Test

In order to investigate the characteristics of the assemblages of porous irregular-shaped fine particles produced in the present Examples for the use as inhalation preparations, a release property evaluation test was performed using a cascade impactor. A cascade impactor is an apparatus which inhales an aerosol through a flow channel where eight stages and a final filter are overlapped, and measures the particle size distribution utilizing inertial impact. As for the fundamental method, the technique described in "Apparatus 3 for Dry Powder Inhalers" in USP30-NF25 Volume 1, p. 220-240, "Physical Tests and Determinations/Aerosols," was employed.

Fine particulate lactose was produced by the following method. Pulverization of lactose (Respitose ML002) was carried out using a jet mill (Type 50-AS, manufactured by Hosokawa Alpine AG), at a supply air pressure of 0.3 MPa and a milling air pressure of 0.1 MPa.

Example 38

10 mg of a powder of fluticasone propionate obtained in the same manner as in Example 31, and 90 mg of the fine particulate lactose were uniformly mixed, and then the mixture was uniformly mixed with 900 mg of lactose for inhalant (Respitose SV003). Thus, 1 g of a preparation of fluticasone propionate for inhalant was obtained.

Comparative Example 20

10 mg of fluticasone propionate obtained in the same manner as in Comparative Example 10, and 90 mg of the fine particulate lactose were uniformly mixed, and then the mixture was uniformly mixed with 900 mg of lactose for inhalant (Respitose SV003). Thus, 1 g of a preparation of fluticasone propionate for inhalant was obtained.

Example 39

20 mg of the preparation of fluticasone propionate for inhalant produced in Example 38 was filled in a device for inhalant (Rotadisk™), and the preparation was inhaled using a cascade impactor (Andersen type) at a flow rate of 28.3 L/min for 5 seconds. Subsequently, the amounts of fluticasone propionate captured at the respective stages of the cascade impactor were quantified by high performance liquid chromatography, and thereby the bronchopulmonary arrival rate was measured. As a result, the bronchopulmonary arrival rate was 14.9%.

Comparative Example 21

20 mg of the preparation of fluticasone propionate for inhalant produced in Comparative Example 20 was filled in a device for inhalant (Rotadisk™), and the preparation was inhaled using a cascade impactor (Andersen type) at a flow rate of 28.3 L/min for 5 seconds. Subsequently, the amounts of fluticasone propionate captured at the respective stages of the cascade impactor were quantified by high performance liquid chromatography, and thereby the bronchopulmonary arrival rate was measured. As a result, the bronchopulmonary arrival rate was 8.2%.

Example 40

20 mg of the preparation of fluticasone propionate for inhalant produced in Example 38 was filled in Japanese Pharmacopoeia No. 2 capsules (Qualicaps™ capsules, manufactured by Qualicaps Co., Ltd.) and mounted in a device for inhalant (Jethaler™, Unisia Jecs Corp.), and the preparation was inhaled using a cascade impactor (Andersen type) at a flow rate of 28.3 L/min for 5 seconds. Subsequently, the amounts of fluticasone propionate captured at the respective stages of the cascade impactor were quantified by high performance liquid chromatography, and thereby the bronchopulmonary arrival rate was measured. As a result, the bronchopulmonary arrival rate was 28.0%.

Comparative Example 22

20 mg of the preparation of fluticasone propionate for inhalant produced in Comparative Example 20 was filled in Japanese Pharmacopoeia No. 2 capsules (Qualicaps™ capsules, manufactured by Qualicaps Co., Ltd.) and mounted in a device for inhalant (Jethaler™, Unisia Jecs Corp.), and the preparation was inhaled using a cascade impactor (Andersen type) at a flow rate of 28.3 L/min for 5 seconds. Subsequently, the amounts of fluticasone propionate captured at the respective stages of the cascade impactor were quantified by high performance liquid chromatography, and thereby the bronchopulmonary arrival rate was measured. As a result, the bronchopulmonary arrival rate was 11.5%.

From the above, it was clear that when the assemblages of porous irregular-shaped fine particles having a particle diameter of about 1 to 20 μm of the present invention are used as an inhalant preparation, the bronchopulmonary arrival rate is enhanced, as compared to the powder fine particles prepared by conventional methods.

12. Rat Oral Administration Test

Test Example 2

The pranlukast hydrate suspension of Example 34 and the pranlukast hydrate suspension of Comparative Example 17 were administered to SD rats (make, five weeks old) using a sonde for oral administration in rats, at a rate of 4 mL/kg (containing 10 mg of pranlukast hydrate in 1 mL). 0.4 mL of blood was collected at 0.5, 1, 2, 4, 6and 8 hours after the administration, and the concentration of the unchanged drug of pranlukast hydrate in blood plasma was measured by HPLC.

TABLE 3

|  | Cmax (μg/mL) | AUC (μg · h/mL) |
| --- | --- | --- |
| Example 34 | 0.333 ± 0.040 | 0.547 ± 0.054 |
| Comparative example 17 | 0.101 ± 0.016 | 0.239 ± 0.013 |

Figure 8:
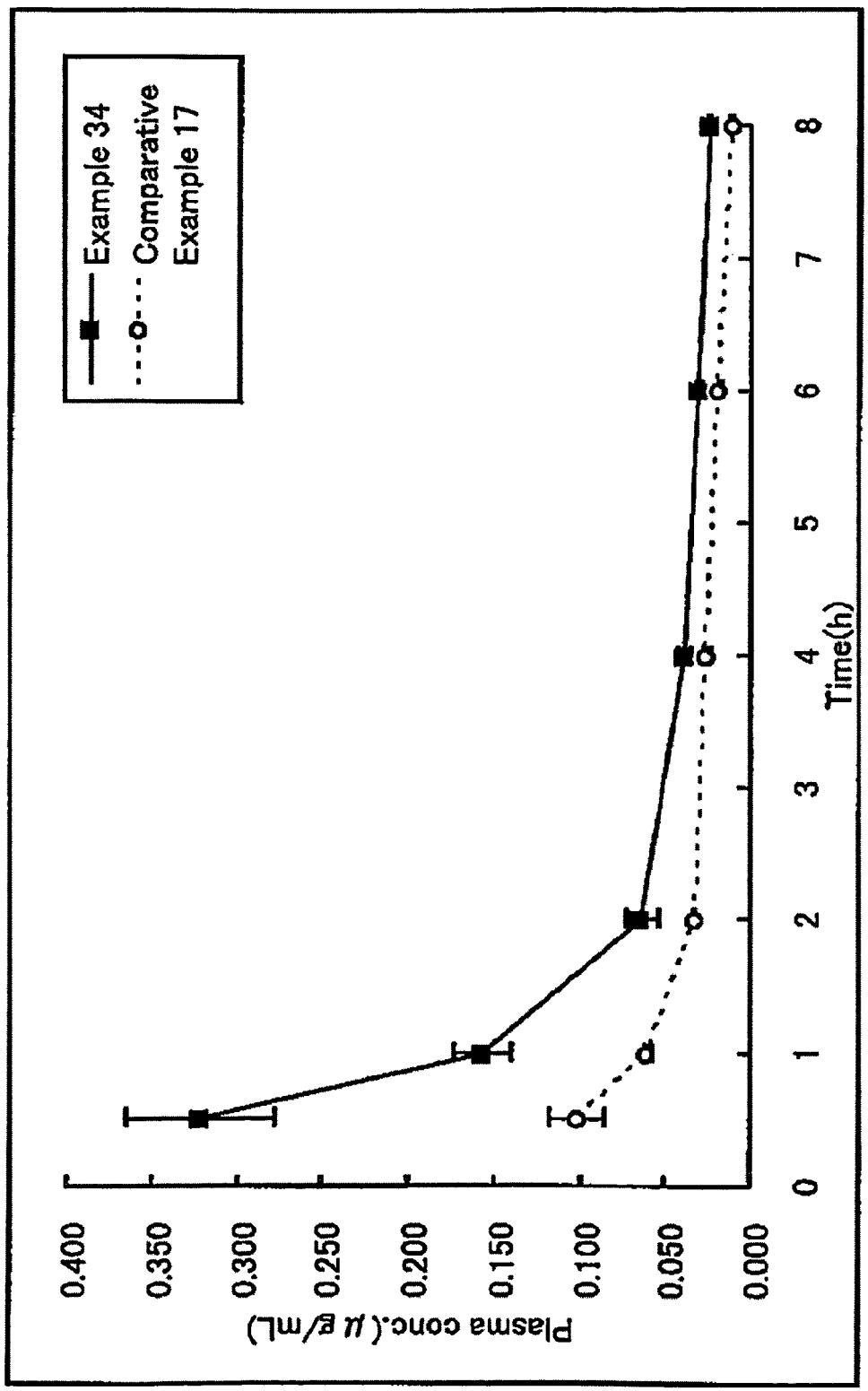
FIG. 8 is a diagram showing the results of a test involving oral administration in rat. In the diagram, the vertical axis represents the drug concentration in the blood serum (μg/mL), and the horizontal axis represents the time elapsed (hour).

The results are shown in Table 3 and FIG. 8. When the fine particles of Example 34 were administered, the Cmax (maximum value of pranlukast hydrate concentration in blood plasma) was 0.333±0.040 μg/mL, and the AUC (area under curve) was 0.547±0.054 μg·hr/mL. When the fine particles of Comparative Example 17 were administered, the Cmas (maximum value of pranlukast hydrate concentration in blood plasma) was 0.101±0.016 µg/mL, and the AUC (area under curve) was 0.239±0.013 µg·hr/mL. From these results, it was shown that in Example 34, the Cmax was about 3.3 times higher and the AUC was about 2.3 times higher as compared to Comparative Example 17, and thus the absorption rate through the digestive tract is improved.

INDUSTRIAL APPLICABILITY

According to the method for producing finely pulverized organic compound particles of the present invention, organic compounds having low solubility in water or the like can be safely and conveniently produced into particles having small average particle diameters that are traditionally unavailable, and therefore, the organic compounds can be used in the fields of medicine and diagnostic medicine.

The invention claimed is:

1. A method for producing poor water solubility organic compound fine particles for medical use comprising:
   mixing a poor water solubility organic compound with at least one physiologically acceptable salt in the amount of 1- to 100-fold with respect to a mass of the poor water solubility organic compound and a physiologically acceptable polyol;
   wet-milling the poor water solubility organic compound by the physiologically acceptable salt; and
   removing the at least one physiologically acceptable salt and the physiologically acceptable polyol after the wet-milling,
   wherein the poor water solubility organic compound has a melting point or a decomposition point in the range of 80 to 350 degrees C., and
   the wet-milled poor water solubility organic compound fine particles maintain its crystal form as the poor water solubility organic compound has before the wet-milling process.

2. A method for producing poor water solubility organic compound fine particles for medical use according to claim 1, wherein the physiologically acceptable polyol includes a viscosity modifier.

3. A method for producing poor water solubility organic compound fine particles for medical use according to claim 2, wherein the viscosity of the polyol is 1000 mPa·s or more at 20 degrees C.

4. A method for producing poor water solubility organic compound fine particles for medical use according to claim 2, wherein the viscosity modifier is citric acid, DL-malic acid, D-sorbitol, D-mannitol, maltitol, maltose, tartaric acid, glucose, erythritol, xylitol, D-xylose, trehalose, fructose, lactic acid, lactose, glycine, urea, maleic acid or malonic acid.

5. A method for producing poor water solubility organic compound fine particles for medical use according to claim 1, wherein the polyol is glycerin, propylene glycol or polyethylene glycol.

6. A method for producing poor water solubility organic compound fine particles for medical use according to claim 1, wherein the at least one physiologically acceptable salt is one or more materials selected from the group consisting of sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate and dipotassium hydrogen phosphate.

7. A method for producing poor water solubility organic compound fine particles for medical use according to claim 1, comprising adding no surface active agent.

8. A method for producing poor water solubility organic compound fine particles for medical use according to claim 1, wherein the poor water solubility organic compound is one or more organic compounds selected from the group consisting of nifedipine, nicardipine, nimodipine, dipyridamole, disopyramide, prazosin hydrochloride, prednisolone, cortisone acetate, dexamethasone, betamethasone, beclometasone dipropionate, fluticasone propionate, budesonide, fluocinolone acetonide, indomethacin, naproxen, ketoprofen, 7-[(3,5-dimethoxy-4-hydroxycinnamoyl)amino]-3-octyloxy-4-hydroxy-1-methyl-2 (1H) -quinolinone, phenytoin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazone, phenprobamate, mequitazine, bisbentiamin, mitomycin C, bicalutamide, paclitaxel, ubenimex, dacarbazine, fluconazole, miconazole, rifampicin, triamcinolone acetonide, clemastine fumarate, pranlukast hydrate, zafirlukast, fenofibrate, dihydroxybenzophenone, dihydrocholesterol, beta-carotene, propyl gallate, cinnamic acid, saccharin, folic acid and maltol.

9. A method for producing poor water solubility organic compound fine particles for medical use according to claim 1, wherein the average diameter of the poor water solubility organic compound fine particles is 600 nm or less.

10. A method for producing poor water solubility organic compound fine particles for medical use according to claim 1, wherein a ratio of the poor water solubility organic compound fine particles with a diameter of 0.2 micron or less is 70% or more.

11. A method for producing poor water solubility organic compound fine particles for medical use according to claim 1, wherein 90% median diameter of the poor water solubility organic compound fine particles is 600 nm or less.

12. A method for producing poor water solubility organic compound fine particles for medical use according to claim 1, wherein the at least one physiologically acceptable salt is removed after the wet-milling.

13. A method for producing poor water solubility organic compound fine particles for medical use according to claim 1, wherein the solubility of the poor water solubility organic compound for medical use in the physiologically acceptable polyol is 10% (mass/volume) or less, and the solubility of the at least one physiologically acceptable salt in the physiologically acceptable polyol is 10% (mass/volume) or less.

14. A method for producing poor water solubility organic compound fine particles for medical use according to claim 1, wherein the at least one physiologically acceptable salt has an average particle size of 5 to 300 µm.

* * * * *